United States Patent [19]

Mittendorf et al.

[11] Patent Number: 5,739,160
[45] Date of Patent: Apr. 14, 1998

[54] CYCLOPENTANE- AND -PENTENE-β-AMINO ACIDS

[75] Inventors: Joachim Mittendorf, Wuppertal; Franz Kunisch, Odenthal; Michael Matzke, Wuppertal; Hans-Christian Militzer, Bergisch Gladbach; Rainer Endermann, Wuppertal; Karl Georg Metzger, Wuppertal; Klaus-Dieter Bremm, Wuppertal; Manfred Plempel, Haan, all of Germany

[73] Assignee: Bayer Aktiengesellschaft, Leverkusen, Germany

[21] Appl. No.: 308,873

[22] Filed: Sep. 19, 1994

Related U.S. Application Data

[63] Continuation of Ser. No. 66,751, May 21, 1993, abandoned.

[30] Foreign Application Priority Data

May 29, 1992 [DE] Germany .................. 42 17 776.6
Jan. 27, 1993 [DE] Germany .................. 43 02 155.7

[51] Int. Cl.$^6$ ................................. A61K 31/21
[52] U.S. Cl. ............. 514/510; 514/530; 514/561; 560/122; 560/115; 560/28; 562/501; 562/504
[58] Field of Search ................. 562/504, 501; 560/122, 115, 28; 514/510, 530, 561

[56] References Cited

PUBLICATIONS

Chemical Abstracts 97:155930, 1982 Brasili et al.
Chemical Abstracts, vol. 55, No. 9 No. 5483.e, rn=103274-87-9, May 1991.
Skinner, Charles; Huddle, John J. Med. Chem. 14(6), 545–6, 1971.
Chemical Abstracts, vol. 55, Column 5483e; 1961.
J. Org. Chem. 1983, 48, pp. 5364–5366.
N.B. Benoton et al., Int.Pept.Prot.Res. 13, 403 (1979).
N.B. Benoton et al., Int.Pept.Prot.Res. 17, 187 (1981).
Th. Greene "Protective Groups in Organic Synthesis", 1.Aufl., J. Wiley&Sons, New York 1981.
Houben–Weyl, "Methoden der organischen Chemie", Bd. X1/1 and X1/2 1974.
Houben–Weyl, "Methoden der organischen Chemie", Bd. XV/1 1957.
J.C. Sheehan and S.L. Ledis, J. Am.Chem. Soc. 95, 875 (1973).
H.J. Gais et al., J. Org. Chem (1989), 54, pp. 5115–5122.
J. Am. Chem. Soc. 1978, 100, pp. 6728–6733.
Chem Ber. 106, (12) 3788–3798 1973.
F.E. Frermanet al., J. Biol. Chem. 255, pp. 2199–2202 (1980); (not 225, 507 (1982).
J. Am. Chem. Soc. 1951, 73, pp. 4286–4289.

*Primary Examiner*—Samuel Barts
*Attorney, Agent, or Firm*—Sprung Kramer Schaefer & Briscoe

[57] ABSTRACT

New Cyclopentane- or cyclopentene-beta-aminoacid derivatives and their isomers, acid additional salts and metal salt complexes have strong antimicrobial and broad-spectrum antimycotic acitivity. As antimycotics they are especially active against dermatophyte, and biphasic fungi. The new compounds are also low toxicity antibacterial agents, effective against Gram positive bacteria, including antibiotic-resistant strains. The new Cyclopentane- or cyclopentene-beta-aminoacid derivatives are useful in human or veterinary medicine for combating dermatomycosis or systemic mycosis or local or systemic bacterial infections. In addition, the new compounds can also be used as preservatives, especially for water, foods, or organic materials such as polymers, lubricants, paints, fibers, leather, paper or wood.

2 Claims, No Drawings

CYCLOPENTANE- AND -PENTENE-β-AMINO ACIDS

This application is a continuation of application Ser. No. 08/066,751, filed May 21, 1993, now abandoned.

The invention relates to cyclopentane- and -pentene-β-amino acids, processes for their preparation and their use as medicaments.

Aminopentenecarboxylic acid derivatives are known from J 63 287,754 A. 2-Oxo-4,5-diphenyl-3,5-cyclopentadiene-1,3-dicarboxylates are additionally known from the publication Chem. Ber. 106 (12), 2788–95.

The compound 2-amino-cyclopentane-carboxylic acid is known from EP-A 0.298.640 as an antimicrobial active compound.

The invention now relates to cyclopentane- and -pentene-β-amino acids of the general formula (I)

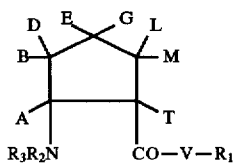

in which

A, B, D, E, G, L, M and T are identical or different and, with the proviso that at least one of the abovementioned substituents is not H, represent hydrogen, halogen, benzyl, hydroxyl or straight-chain or branched alkyl having up to 8 carbon atoms, which is optionally monosubstituted or disubstituted by identical or different halogen, hydroxyl, phenyl, benzyloxy or carboxyl substituents or by straight-chain or branched alkoxy, acyl- or alkoxycarbonyl each having up to 6 carbon atoms or by a group of the formula —NR$^4$R$^5$, in which R$^4$ and R$^5$ are identical or different and denote hydrogen, phenyl or straight-chain or branched alkyl having up to 6 carbon atoms, or B and D, E and G or L and M in each case together represent a radical of the formula

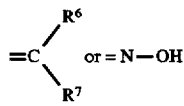

in which

R$^6$ and R$^7$ are identical or different and denote hydrogen, halogen or straight-chain or branched alkyl, alkoxy or oxyacyl each having up to 8 carbon atoms, benzyl or phenyl, or E and G and/or B and D together represent the radical of the formula =O or =S, or B, D, E and G or E, G, L and M in each case together form a radical of the formula

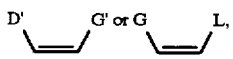

in which

D' and G' have the abovementioned meaning of D and G, but do not simultaneously denote hydrogen and G and L have the abovementioned meaning R$^2$ represents hydrogen or represents an amino-protective group, or represents straight-chain or branched alkyl having up to 8 carbon atoms, which is optionally monosubstituted or disubstituted by identical or different hydroxyl or formyl substituents or by straight-chain or branched acyl having up to 6 carbon atoms or by phenyl or benzoyl, each of which is optionally substituted up to 2 times by identical or different halogen, nitro or cyano substituents, or by straight-chain or branched alkyl having up to 6 carbon atoms, or represents straight-chain or branched acyl having up to 8 carbon atoms, or represents benzoyl which is optionally substituted as described above, or represents a group of the formula —SO$_2$R$^8$, in which R$^8$ denotes straight-chain or branched alkyl having up to 8 carbon atoms, benzyl or phenyl, where the latter are optionally substituted up to 3 times by identical or different halogen, hydroxyl, nitro, cyano, trifluoromethyl or trifluoromethoxy substituents or by straight-chain or branched alkyl, alkoxy or alkoxycarbonyl each having up to 6 carbon atoms, carboxyl or by the abovementioned group —NR$^4$R$^5$, in which R$^4$ and R$^5$ have the abovementioned meaning, represents phenyl which is optionally substituted up to 3 times by identical or different halogen, hydroxyl, nitro, trifluoromethyl, trifluoromethoxy, straight-chain or branched alkyl, acyl, alkoxy or alkoxycarbonyl substituents each having up to 6 carbon atoms or by a group of the formula —NR$^4$R$^5$ or —SO$_2$R$^8$, in which R$^4$, R$^5$ and R$^8$ have the abovementioned meaning, or represents an amino acid residue of the formula

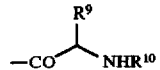

in which

R$^9$ denotes cycloalkyl having 3 to 8 carbon atoms or aryl having 6 to 10 carbon atoms or hydrogen, or denotes straight-chain or branched alkyl having up to 8 carbon atoms, where the alkyl is optionally substituted by cyano, methylthio, hydroxyl, mercapto or guanidyl or by a group of the formula —NR$^{11}$R$^{12}$ or R$^{13}$—OC—, in which R$^{11}$ and R$^{12}$ independently of one another represent hydrogen, straight-chain or branched alkyl having up to 8 carbon atoms or phenyl, and R$^{13}$ denotes hydroxyl, benzyloxy, alkoxy having up to 6 carbon atoms or the abovementioned group —NR$^{10}$R$^{11}$, or the alkyl is optionally substituted by cycloalkyl having 3 to 8 carbon atoms or by aryl having 6 to 10 carbon atoms, which is in turn substituted by hydroxyl, halogen, nitro or alkoxy having up to 8 carbon atoms or by the group —NR$^{11}$R$^{12}$, in which R¹¹ and R¹² have the abovementioned meaning, and R¹⁰ denotes hydrogen or an amino-protective group R³ represents hydrogen or straight-chain or branched alkyl having up to 8 carbon atoms, which is optionally substituted by phenyl, or R² and R³ together represent the radical of the formula =CHR¹⁴, in which R¹⁴ denotes hydrogen or straight-chain or branched alkyl having up to 8 carbon atoms, which is optionally substituted by halogen, hydroxyl, phenyl or carboxyl or by straight-chain or branched alkoxy or alkoxycarbonyl each having up to 6 carbon atoms, V represents an oxygen or sulphur atom or the —NH group, R¹ represents hydrogen or straight-chain or branched alkyl having up to 8 carbon atoms or phenyl, where the latter are optionally substituted up to 3 times by identical or different hydroxyl, halogen, nitro, cyano, carboxyl, trifluoromethyl or trifluoromethoxy substitutents, by straight-chain or branched alkoxy, in the case of phenyl also by alkyl, acyl or alkoxycarbonyl each having up to 6 carbon atoms or by a group of the formula —NR⁴R⁵ or —SO₂R⁸, in which R⁴, R⁵ and R⁸ have the abovementioned meaning, or in the case in which V represents the —NH group, R¹ represents the group of the formula —SO₂R⁸, in which R⁸ has the abovementioned meaning, if appropriate in an isomeric form, and their acid addition salts and metal salt complexes.

The compounds according to the invention can also be present in the form of their salts. In general, salts with organic or inorganic bases or acids may be mentioned here.

The acids which can be adapted are preferably hydrohalic acids, such as, for example, hydrochloric acid and hydrobromic acid, in particular hydrochloric acid, and also phosphoric acid, nitric acid, sulphuric acid, mono- and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid as well as sulphonic acids, such as, for example, p-toluenesulphonic acid, 1,5-naphthalenedisulphonic acid or camphorsulphonic acid.

Physiologically acceptable salts can also be metal or ammonium salts of the compounds according to the invention which have a free carboxyl group. Those particularly preferred are, for example, sodium, potassium, magnesium or calcium salts, as well as ammonium salts which are derived from ammonia, or organic amines such as, for example, ethylamine, di- or triethylamine, di- or triethanolamine, dicyclohexylamine, dimethylaminoethanol, arginine, lysine, ethylenediamine or phenethylamine.

Amino-protective groups in the context of the invention are the customary amino-protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl, allyloxycarbonyl, vinyloxycarbonyl, 2-nitrobenzyloxycarbonyl, 3,4,5-trimethoxybenzyloxycarbonyl, phthaloyl, 2,2,2-trichloroethoxycarbonyl, 2,2,2-trichloro-tert-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, dinitrobenzyl, 4-nitrophenyl or 2-nitrophenylsulphenyl.

The compounds according to the invention can exist in stereoisomeric forms, which behave, for example, either as image and mirror image (enantiomers), or which do not behave as image and mirror image (diastereomers), or as a diastereomer mixture or as pure cis- or trans-isomers respectively. The invention relates both to the antipodes, racemic forms and diastereomer mixtures as well as to the pure isomers. Like the diastereomers, the racemic forms can be separated in a known manner into the stereoisomerically uniform constituents. Separation into the stereoisomerically uniform compounds is carried out, for example, by means of a chromatographic resolution of diastereomeric esters and amides on optically active phases. Crystallisation of diastereomeric salts is additionally possible.

Preferred compounds of the general formula (I) are those in which

A, B, D, E, G, L, M and T are identical or different and, with the proviso that at least one of the abovementioned substituents is not H, represent hydrogen, halogen, benzyl, hydroxyl or straight-chain or branched alkyl having up to 6 carbon atoms, which is optionally monosubstituted or disubstituted by identical or different halogen, benzyloxy or hydroxyl substituents, by straight-chain or branched alkoxy, acyl or alkoxycarbonyl each having up to 4 carbon atoms or by a group of the formula —NR⁴R⁵, in which R⁴ and R⁵ are identical or different and denote hydrogen or straight-chain or branched alkyl having up to 4 carbon atoms, or B and D, E and G or L and M in each case together represent a radical of the formula $$=C{\overset{\displaystyle R^6}{\underset{\displaystyle R^7}{\diagup\!\!\!\diagdown}}} \quad \text{or} \quad -N-OH,$$

in which

R⁶ and R⁷ are identical or different and denote hydrogen, fluorine, chlorine or bromine, or straight-chain or branched alkyl having up to 6 carbon atoms, benzyl or phenyl, or E and G and/or B and D together represent the radical of the formula =O or =S, or B, D, E and G or E, G, L and M in each case together form a radical of the formula

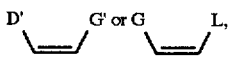

in which

D' and G' have the abovementioned meaning of D and G, but do not simultaneously represent hydrogen
and G and L have the abovementioned meaning, $R^2$ represents hydrogen or represents Boc, benzyl, benzyloxycarbonyl, allyloxycarbonyl or 9-fluorenylmethoxycarbonyl (Fmoc), or represents straight-chain or branched alkyl having up to 6 carbon atoms, which is optionally substituted by hydroxyl or formyl or by straight-chain or branched acyl having up to 4 carbon atoms or by phenyl or benzoyl, each of which is optionally substituted by halogen, nitro or cyano, or by straight-chain or branched alkyl having up to 4 carbon atoms, or represents straight-chain or branched acyl having up to 6 carbon atoms or benzoyl which is optionally substituted as described above, or represents a group of the formula —$SO_2R^8$, in which $R^8$ denotes straight-chain or branched alkyl having up to 6 carbon atoms, phenyl or benzyl, where the latter is optionally substituted up to 2 times by identical or different halogen, hydroxyl, nitro, cyano, trifluoromethyl or trifluoromethoxy substituents or by straight-chain or branched alkyl or alkoxy each having up to 4 carbon atoms or by the abovementioned group of the formula —$NR^4R^5$, in which $R^4$ and $R^5$ have the abovementioned meaning, represents phenyl which is optionally substituted up to 2 times by identical or different halogen, hydroxyl, nitro, trifluoromethyl, trifluoromethoxy, straight-chain or branched alkyl, acyl, alkoxy or alkoxycarbonyl substituents each having up to 4 carbon atoms or by a group of the formula —$NR^6R^7$ or —$SO_2R^8$, in which $R^6$, $R^7$ and $R^8$ have the abovementioned meaning, or represents an amino acid residue of the formula

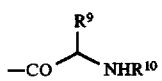

in which $R^9$ denotes hydrogen, straight-chain or branched alkyl having up to 6 carbon atoms or benzyl
and $R^{10}$ denotes hydrogen, benzyloxycarbonyl, Fmoc or tert-butoxycarbonyl, $R^3$ represents hydrogen or straight-chain or branched alkyl having up to 6 carbon atoms or benzyl, or $R^2$ and $R^3$ together represent the radical of the formula =$CHR^{14}$, in which $R^{14}$ denotes hydrogen or straight-chain or branched alkyl having up to 6 carbon atoms, which is optionally substituted by halogen or hydroxyl, or by straight-chain or branched alkoxy or alkoxycarbonyl each having up to 4 carbon atoms, V represents an oxygen or sulphur atom or the —NH group, represents hydrogen or straight-chain or branched alkyl having up to 6 carbon atoms or phenyl, where the latter are optionally substituted up to 2 times by identical or different hydroxyl, halogen, nitro, cyano, trifluoromethyl or trifluoromethoxy substituents, by straight-chain or branched alkoxy, acyl or alkoxycarbonyl each having up to 4 carbon atoms or by a group of the formula —$NR^4R^5$ or —$SO_2R^8$, in which $R^4$, $R^5$ and $R^8$ have the abovementioned meaning, or in the case in which V represents the —NH group, $R^1$ represents the group of the formula —$SO_2R^8$, in which $R^8$ has the abovementioned meaning, if appropriate in an isomeric form, and their acid addition salts and metal salt complexes.

Particularly preferred compounds of the general formula (I) are those in which

A, B, D, E, G, L, M and T are identical or different and, with the proviso that at least one of the abovementioned substituents is not H, represent hydrogen, fluorine, chlorine, bromine, benzyl or hydroxyl, or represent straight-chain or branched alkyl having up to 4 carbon atoms, which is optionally monosubstituted or disubstituted by identical or different hydroxyl or benzyloxy substituents, or B and D, E and G or L and M in each case together represent a radical of the formula

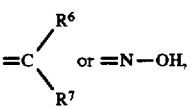

in which $R^6$ and $R^7$ are identical or different and denote hydrogen, fluorine, chlorine, bromine or straight-chain or branched alkyl having up to 4 carbon atoms or phenyl, or E and G and/or B and D together represent the radical of the formula =O or =S, or B, D, E and G or E, G, L and M in each case together form a radical of the formula

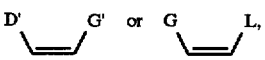

in which

D' and G' have the abovementioned meaning of D and G, but do not simultaneously represent hydrogen, G and L are identical or different and denote hydrogen or methyl, $R^2$ represents hydrogen, allyloxycarbonyl, benzyl, Boc or Fmoc, or represents straight-chain or branched alkyl having up to 4 carbon atoms, or represents straight-chain or branched acyl having up to 4 carbon atoms or represents a group of the formula —SO$_2$R$^8$, in which R$^8$ denotes straight-chain or branched alkyl having up to 4 carbon atoms, phenyl or benzyl, where the latter are optionally substituted by hydroxyl, fluorine, chlorine, bromine, nitro, cyano, methyl, ethyl or methoxy, or represents an amino acid residue of the formula

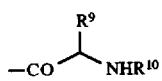

in which

R$^9$ denotes hydrogen, straight-chain or branched alkyl having up to 4 carbon atoms or benzyl and R$^{10}$ denotes hydrogen, tert-butoxycarbonyl or Fmoc, R$^3$ represents hydrogen or represents straight-chain or branched alkyl having up to 4 carbon atoms, or R$^2$ and R$^3$ together represent the radical of the formula =CHR$_{14}$ in which R$^{14}$ denotes hydrogen or straight-chain or branched alkyl having up to 4 carbon atoms, V represents an oxygen or a sulphur atom or the —NH group, R$^1$ represents hydrogen or straight-chain or branched alkyl having up to 4 carbon atoms or phenyl, where the latter are optionally substituted by fluorine, chlorine, bromine, nitro, cyano, methoxy or ethoxy or by a group of the formula —NR$^4$R$^5$ or —SO$_2$R$^8$, in which R$^4$ and R$^5$ are identical or different and denote hydrogen, methyl or ethyl and R$^8$ has the abovementioned meaning, or in the case in which V represents the —NH group, R$^1$ represents the group of the formula —SO$_2$R$^8$, in which R$^8$ has the abovementioned meaning, if appropriate in an isomeric form, and their acid addition salts and metal salt complexes.

Additionally, processes for the preparation of the compounds of the general formula (I) according to the invention have been found, characterised in that

[A] compounds of the general formula (II)

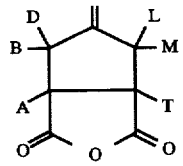

in which

A, B, D, L, M and T have the abovementioned meaning, are converted in organic solvents, preferably dioxane, first with (C$_1$–C$_3$)-trialkylsilyl azides, then with ethers, in the presence of water, to the compounds of the general formula (III)

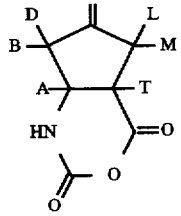

in which

A, B, D, L, M and T have the abovementioned meaning, and in a next step the products are reacted with acids, preferably hydrochloric acid, with ring opening to give the compounds of the general formula (Ia)

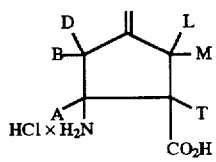

in which

A, B, D, L, M and T have the abovementioned meaning, and if appropriate an elimination with acids, preferably hydrochloric acid, is added, or

[B] compounds of the general formula (IV)

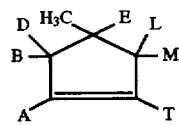

in which

A, B, D, E, L, M and T have the abovementioned meaning, are converted by reaction with chlorosulphonyl isocyanate first to the compounds of the general formula (V)

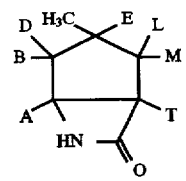

in which

A, B, D, E, L, M and T have the abovementioned meaning, and then the amine and carboxyl function are set free with acids, preferably hydrochloric acid, with ring opening, or

[C] compounds of the general formula (VI)

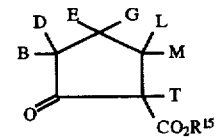

in which

B, D, E, G, L, M and T have the abovementioned meaning, and

R$^{15}$ represents C$_1$–C$_4$-alkyl, are converted by reaction with amines of the general formula (VII)

$$H_2N-R^{16} \quad (VII)$$

in which
R$^{16}$ represents benzyl which is optionally substituted by halogen, NO$_2$, cyano or C$_1$–C$_4$-alkyl or represents the radical of the formula —CH(C$_6$H$_4$-pOCH$_3$)$_2$.

in organic solvents, if appropriate in the presence of a base, to the compounds of the general formula (VIII)

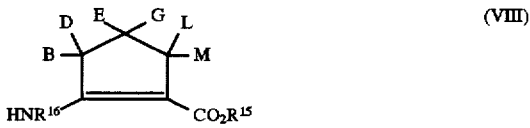

in which
B, D, E, G, L, M, R$^{15}$ and R$^{16}$ have the abovementioned meaning,
and then by double hydrogenation first the double bond is reduced, then the amine function is set free and in a last step the carboxylic acid esters are hydrolysed using acids, and fundamentally the substituents A–T are derivatised, if appropriate with prior blockage of the amine function, by reaction of the protective groups according to customary methods, for example by oxidation, reduction or alkylation, and in the case of the acids the esters are hydrolysed according to customary methods, and in the case of the other definitions mentioned above for V and R$^1$, they are likewise derivatised according to customary methods, such as, for example, amidation, sulphonation or sulphoamidation, if appropriate in the presence of auxiliaries such as catalysts and dehydrating agents, starting from the corresponding carboxylic acids, if appropriate with prior activation, and in the case of the pure enantiomers a resolution is carried out.

The process according to the invention can be illustrated by way of example by the following reaction scheme:

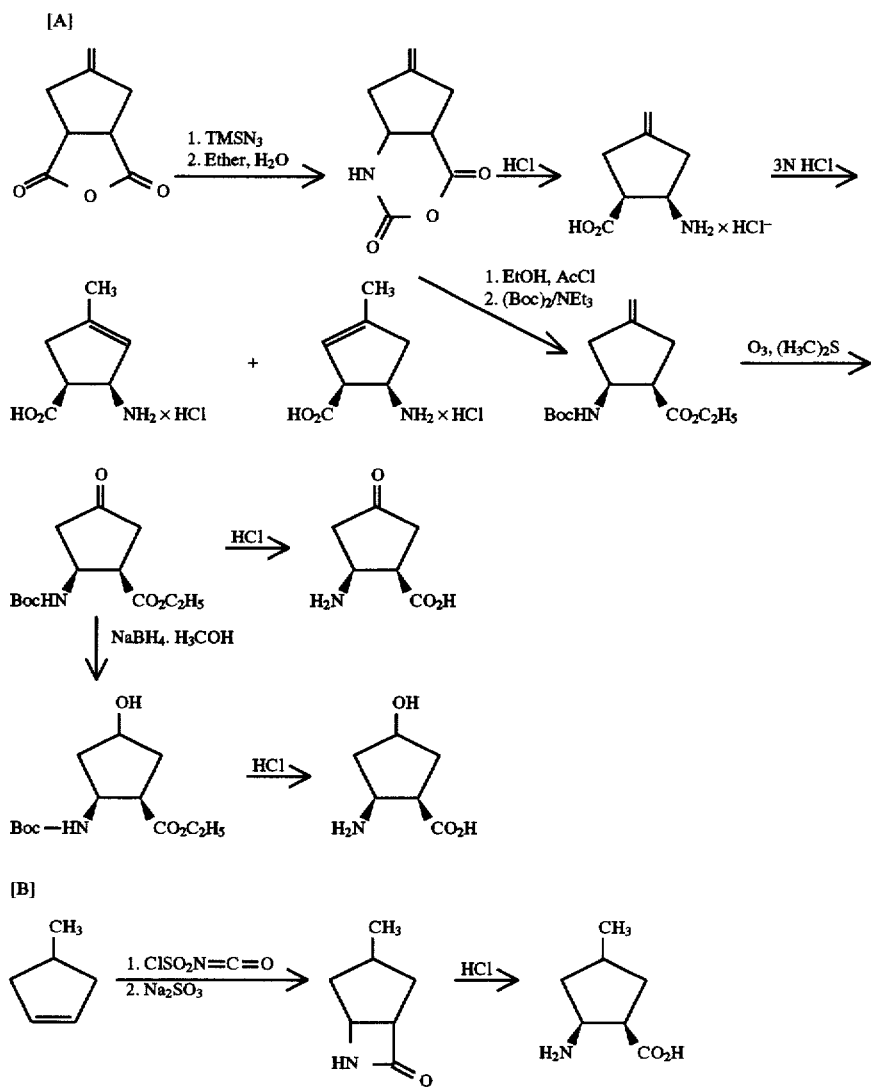

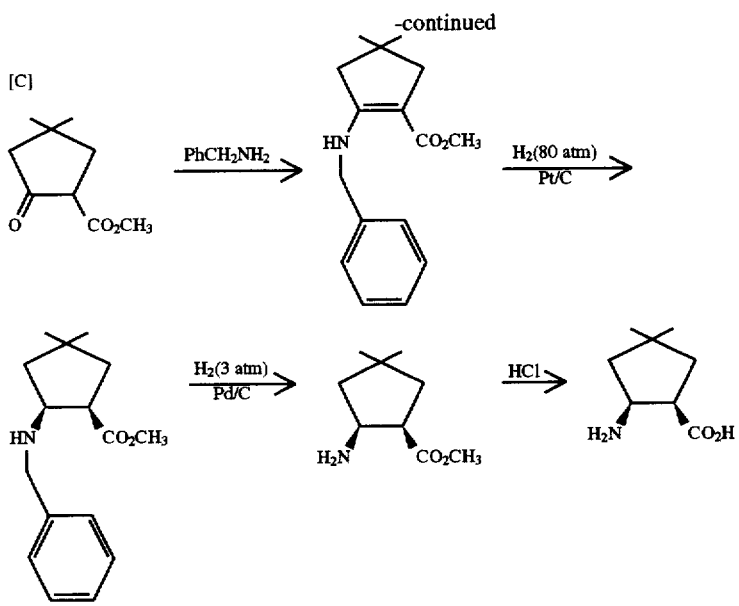

Suitable solvents for the individual steps of processes [A], [B] and [C] are water and all inert organic solvents which do not change under the reaction conditions. These preferably include alcohols such as methanol, ethanol, propanol or isopropanol, ethers such as diethyl ether, dioxane, diisopropyl ether, tetrahydrofuran, glycol monomethyl ether or glycol dimethyl ether, or chlorinated hydrocarbons, such as chloroform or methylene chloride, or amides such as dimethylformamide, dimethylacetamide or hexamethylphosphoramide, or glacial acetic acid, dimethyl sulphoxide, acetonitrile or pyridine. Those preferred for the individual steps are diisopropyl ether, diethyl ether, dioxane, methanol, ethanol and dichloromethane.

The reaction temperatures can be varied within a relatively wide range. In general, the reaction is carried out between −78° C. and +150° C., preferably between −10° C. and +100° C.

The reactions can be carried out at normal pressure, but also at elevated or reduced pressure (for example 0.5 to 80 bar). In general, the reactions are carried out at normal pressure or at an elevated pressure of 3 to 80 bar.

When carrying out process variants [A], [B] and [C] according to the invention, any desired ratio of the substances participating in the reaction can be used. In general, however, the reaction is carried out using molar amounts of the reactants. The substances according to the invention are preferably isolated and purified by distilling off the solvent in vacuo and recrystallising the residue, which may only be obtained crystalline after ice-cooling, from a suitable solvent. In some cases, it may be necessary to purify the compounds according to the invention by chromatography.

Suitable oxidising agents are, for example, hydrogen peroxide, sodium periodate, peracids such as m-chloroperbenzoic acid or potassium permanganate. Hydrogen peroxide, m-chloroperbenzoic acid and sodium periodate are preferred.

Suitable bases are organic amines (trialkyl($C_1$–$C_6$) amines) such as, for example, triethylamine or heterocycles such as pyridine, methylpiperidine, piperidine or morpholine. Triethylamine is preferred.

The acids employed for the ring opening (V) are in general mineral acids. Those preferred here are hydrochloric acid, hydrobromic acid, sulphuric acid, phosphoric acid or else mixtures of the acids mentioned. Hydrochloric acid is preferred.

Suitable acids for the deblocking (III) are $C_1$–$C_6$-carboxylic acids such as, for example, acetic acid or propionic acid. Acetic acid is preferred.

The acid is in general employed in an amount from 2 mol to 30 mol, preferably from 5 mol to 15 mol, in each case relative to 1 mol of the compounds of the general formulae (III) and (V).

The carboxylic acid esters are hydrolysed according to customary methods by treating the esters in inert solvents with customary bases, it being possible to convert the initially formed salts into the free carboxylic acids by treating with acid.

The hydrolysis of the carboxylic acid esters can also be carried out using one of the abovementioned acids.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium ethoxide, potassium methoxide or potassium tert-butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base or the acid is in general employed in an amount from 1 to 3 mol, preferably from 1 to 1.5 mol, relative to 1 mol of the ester. Molar amounts of the reactants are preferably used.

When carrying out the reaction, in the first step the salts of the compounds according to the invention are formed as intermediates which can be isolated. The acids according to the invention are obtained by treating the salts with customary inorganic acids. These preferably include mineral acids such as, for example, hydrochloric acid, hydrobromic acid, sulphuric acid or phosphoric acid. It has proven advantageous in the preparation of the carboxylic acids to acidify the basic reaction mixture from the hydrolysis in a second step without isolation of the salts. The acids can then be isolated in a customary manner.

By way of example of the abovementioned derivatisation possibilities, the amidation and sulphonation or sulphonamidation will be illustrated here.

The amidation is in general carried out in inert solvents in the presence of a base and of a dehydrating agent.

Suitable solvents here are inert organic solvents which do not change under the reaction conditions. These include halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or mineral oil fractions, nitromethane, dimethylformamide, acetonitrile or hexamethylphosphoramide. It is also possible to employ mixtures of the solvents. Dichloromethane is particularly preferred.

Suitable bases for the amidation are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alkoxides such as, for example, sodium methoxide or ethoxide, potassium methoxide or ethoxide or potassium tert-butoxide, or organic amines such as benzyltrimethylammonium hydroxide, tetrabutylammonium hydroxide, pyridine, triethylamine or N-methylpiperidine.

The amidation is in general carried out in a temperature range from 0° C. to 150° C., preferably at 25° C. to 40° C.

The amidation is in general carried out at normal pressure. However, it is also possible to carry out the process at reduced pressure or at elevated pressure (for example in a range from 0.5 to 5 bar).

Suitable dehydrating reagents are carbodiimides such as, for example, diisopropyl carbodiimide, dicyclohexylcarbodiimide or N-(3-dimethylaminopropyl)-N'ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The sulphonation or sulphoamidation is carried out in the abovementioned inert solvents, if appropriate using the bases and dehydrating agents also mentioned above.

The sulphonation and sulphoamidation are in general carried out at normal pressure. However, it is also possible to carry out the processes at reduced pressure or elevated pressure (for example in a range from 0.5 to 5 bar).

The sulphonation and the sulphoamidation are in general carried out in a temperature range from 0° C. to +150° C., preferably from +25° C. to +40° C.

The commercially available amines and their derivatives known from the literature are in general suitable for the amidation.

The sulphonation and sulphoamidation are in general also carried out using the customary sulphonic acids and their activated derivatives.

The esterification of the acids is carried out by a customary method by reacting the acids with the appropriate alcohols, if appropriate in one of the abovementioned solvents in the presence of a catalyst. This alcohol is preferably also employed as a solvent.

Catalysts which can be employed are inorganic acids, such as, for example, sulphuric acid or inorganic acid chlorides, such as, for example, thionyl chloride, or p-toluenesulphonic acid.

In general, 0.01 to 1, preferably 0.05 to 0.5, mol of catalyst is employed relative to 1 mol of reactant.

Both the esterification and the amidation can optionally proceed via activated stages of the carboxylic acids, such as, for example, acid halides, which are prepared from the corresponding acid by reaction with thionyl chloride, phosphorus trichloride, phosphorus pentachloride, phosphorus tribromide or oxalyl chloride. The acid addition salts of the compounds of the formula (I) can be obtained in a simple manner by customary salt formation methods, for example by dissolving a compound of the formula (I) in a suitable solvent and adding the acid, for example hydrochloric acid, and isolated in a known manner, for example by filtering off, and optionally purified by washing with an inert organic solvent.

The removal of the amino-protective groups is carried out in a manner known per se.

The conversion of double bonds to carbonyl functions is carried out by ozonolysis and reduction of the ozonides with reducing agents such as, for example, dimethyl sulphoxide, zinc or ($C_1$–$C_3$)-trialkylphosphines.

The reduction of alkoxycarbonyl compounds or aldehydes to the corresponding alcohols is in general carried out using hydrides, such as sodium borohydride or potassium borohydride, preferably using sodium borohydride in inert solvents such as ethers, hydrocarbons or alcohols or mixtures thereof, preferably in ethers such as, for example, diethyl ether, tetrahydrofuran or dioxane, or alcohols such as ethanol, in the case of the ketones and aldehydes preferably using sodium borohydride in ethanol, in a temperature range from 0° C. to +150° C., preferably from +20° C. to +100° C., at normal pressure.

The introduction of double bonds is in general carried out by conversion of the alcohols to the corresponding mesylates, tosylates, bromides, iodides or arylselenyl compounds, preferably using 2-nitrophenyl selenocyanate and tri-n-butylphosphine, and subsequent elimination of the leaving groups using bases, preferably using one of the abovementioned organic amines, or by elimination of the selenyl groups by oxidation, preferably using $H_2O_2$ in $H_2O$/THF.

Suitable solvents for the alkylation are customary organic solvents which do not change under the reaction conditions. These preferably include ethers such as diethyl ether, dioxane, tetrahydrofuran or glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

The alkylation is carried out in the abovementioned solvents at temperatures from 0° C. to +150° C., preferably at room temperatures up to +100° C., at normal pressure. The hydrogenations (reductions, removals of protective groups) are in general carried out in one of the abovementioned solvents such as alcohols, for example methanol, ethanol or propanol, in the presence of a noble metal catalyst such as platinum, platinum/C, palladium, palladium on animal carbon or Raney nickel, in the case of the double bond of the compound of the general formula (VIII) preferably using $H_2$/platinum or using $H_2$/palladium.

Catalysts used are in general acids. These preferably include inorganic acids such as, for example, hydrochloric acid or sulphuric acid, or organic sulphonic or carboxylic acids such as, for example, methanesulphonic acid, ethanesulphonic acid, benzenesulphonic acid, toluenesulphonic acid, acetic acid or propionic acid.

The hydrogenations can be carried out at normal, elevated or reduced pressure (for example 0.5–5 bar).

The catalysts and bases are in general employed in an amount from 0 mol to 10 mol, preferably from 1.5 mol to 3.5 mol, in each case relative to 1 mol of the compounds of the general formulae (IV), (V), (VI) and (VIII).

The acid is in general employed in an amount from 2 mol to 30 mol, preferably from 5 mol to 15 mol, in each case relative to 1 mol of the compounds of the general formulae (IV), (V), (VI) and (VIII).

The compounds of the general formula (II) are in the main new and can be prepared, for example, by first setting free, in compounds of the general formula (IX)

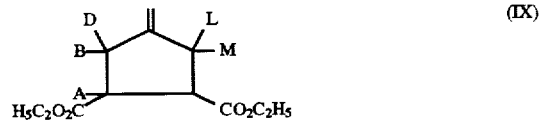

in which

A, B, D, L, M and T have the abovementioned meaning, the corresponding dicarboxylic acids by basic hydrolysis, preferably using lithium hydroxide/$H_2O$ in one of the abovementioned solvents, preferably tetrahydrofuran, then reacting with propionic anhydride.

The compounds of the general formula (IX) are known per se or can be prepared by customary methods [cf. H. J. Gais, J. Org. Chem. 1989, 54, 5115].

The compounds of the general formulae (V) and (VIII) are new and can be prepared, for example, by the abovementioned processes.

The compounds of the general formula (IV) are known per se or can be prepared by a customary method.

The compounds of the general formula (VI) are in the main known or can be prepared by methods known from the literature [cf. JOC, 1983, 48, 5364; JACS, 1951, 73, 4286; JACS, 1978, 100 6728].

The amines of the general formula (VII) are known and can be prepared by customary methods or are commercially available.

The compounds of the general formula (Ia) are new and can be prepared by the abovementioned process.

Starting from the racemates, the pure enantiomers can be obtained by first blocking the amine function with a protective group, preferably Fmoc, then after reaction with chiral amines, such as, for example, phenethylamine or (−)-quinine, preferably with phenethylamine, crystallising the corresponding diastereomeric salts and in a last step removing the protective group, for example with liquid ammonia.

The process can be illustrated by way of example by the following reaction scheme:

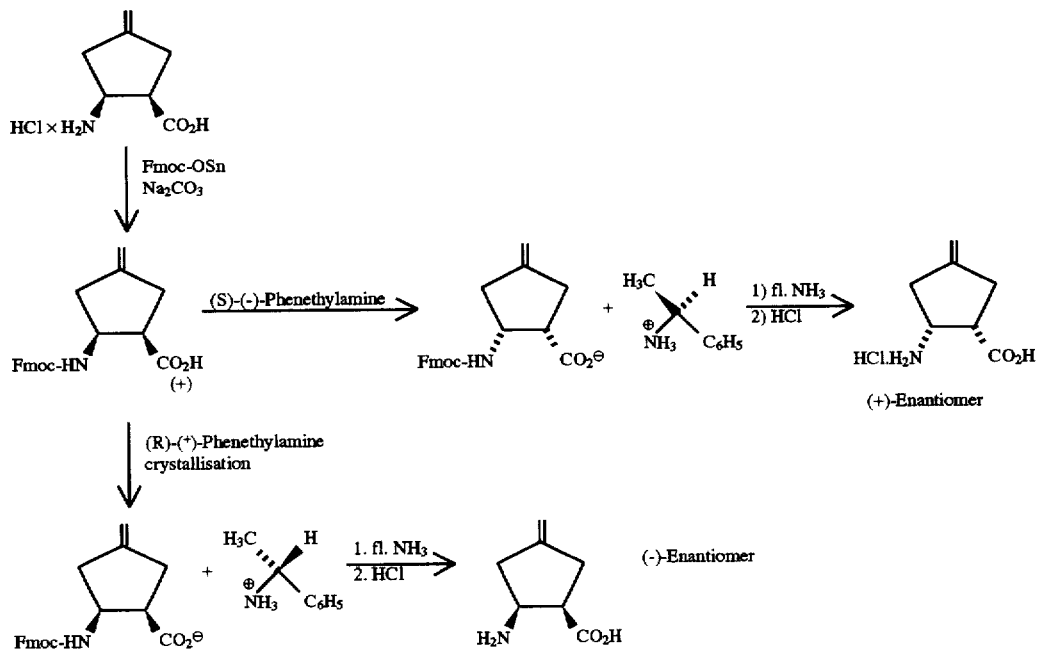

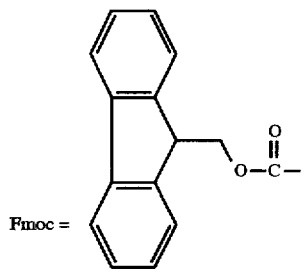

Fmoc =

The above preparation processes are only given for clarification. The preparation of the compounds of the general formulae (I) and (Ia) according to the invention is not restricted to these processes, and any modification of these processes can be used for the preparation in the same way.

The compounds of the general formula (I) according to the invention and their acid addition salts have strong antimicrobial and antimycotic actions. Thus they have, for example, a very wide spectrum of antimycotic action, in particular against dermatophytes and yeast fungi as well as biphasic fungi, for example against Candida species such as *Candida albicans*, Epidermophyton species such as *Epidermophyton floccosum*, Aspergillus species such as *Aspergillus niger* and *Aspergillus fumigatus*, Trichophyton species such as *Trichophyton mentagrophytes*, Microsporon species such as *Microsporon felineum* as well as Torulopsis species, such as *Torulopsis glabrata*. The list of these microorganisms under no circumstances represents a limitation of the microorganisms which can be controlled, but is only of illustrative character.

TABLE A

| Ex. No. | Dose [mg/kg, 2 × daily] | Administration | Number of surviving animals |
|---|---|---|---|
| Control |  |  | 1/10 |
| 1 | 25.50 | sc,po | 7/10 |
| 2 | 25 | sc,po | 9/10 |
| 9 | 25 | sc | 3/10 |
| 32 | 10 | sc,po | 10/10 |
| 37 | 10 | sc,po | 10/10 |
| 41 | 50 | po | 7/10 |
| 45 | 25 | po | 10/10 |
| 46 | 25 | po | 8/10 |
| 47 | 25 | po | 8/10 |
| 49 | 10 | po | 8/10 |

Indication areas in human medicine which can be mentioned by way of example are:

Dermatomycoses and systemic mycoses caused by *Trichophyton mentagrophytes* and other Trichophyton species, Microsporon species and *Epidermophyton floccosum*, yeast fungi and biphasic fungi as well as mould fungi.

Indication areas in veterinary medicine which can be mentioned by way of example are:

All dermatomycoses and systemic mycoses, in particular those which are caused by the abovementioned pathogens.

The compounds according to the invention moreover show an unforeseeable, useful spectrum of antibacterial activity.

They have low toxicity and are antibacterially active against gram-positive organisms, in particular also against those microorganisms which are resistant to various antibiotics, such as, for example, penicillins, cephalosporins, tetracyclines, macrolides and quinolones.

These useful properties make possible their use as chemotherapeutic active compounds in medicine and as substances for the preservation of inorganic and organic materials, in particular of organic materials of all types, for example polymers, lubricants, dyes, fibres, leather, paper and wood, of foodstuffs and of water.

Using the compounds according to the invention, gram-positive bacteria can be combated, and the diseases caused by these pathogens can be prevented, ameliorated and/or cured. They are therefore particularly highly suitable for the prophylaxis and chemotherapy of local and systemic infections in human and veterinary medicine which are caused by these pathogens.

Thus, a logarithmically growing *S. aureus* 133 cutlture was diluted with physiological saline solution so that $1 \times 10^8$ bacteria could be injected intraperitoneally into mice in 0.25 ml. The treatment of the infected animals took place 0.5 and 3 hours after infection. The survival of the mice was recorded up to the 6th day after infection.

| Example 32 | % surviving on the | | | | | |
|---|---|---|---|---|---|---|
|  | 1st | 2nd | 3rd | 4th | 5th | 6th day |
| Dose group |  |  |  |  |  |  |
| 2 × 25 mg/kg | 100 | 50 | 50 | 50 | 50 | 50 |
| 2 × 50 mg/kg | 100 | 67 | 50 | 50 | 50 | 50 |
| 2 × 100 mg/kg | 100 | 100 | 83 | 83 | 83 | 83 |
| Infection control | 33 | 17 | 17 | 17 | 17 | 17 |

Example 32 shows a dose-dependent therapeutic effect compared to the untreated infection control.

| Example No. | % Surviving on the | | % Surviving infection control | |
|---|---|---|---|---|
|  | 1st day | 2nd day | 1st day | 2nd day |
| 2 | 83 | 50 | 33 | 16 |
| 5 | 67 | 33 | 33 | 16 |
| 16 | 83 | 50 | 33 | 16 |
| 17b | 50 | 50 | 33 | 16 |
| 24 | 83 | 33 | 33 | 16 |
| 37 | 100 | 50 | 67 | 16 |

The novel active compound can be converted in a known manner into the customary formulations, such as tablets, coated tablets; capsules, pills, granules, suppositories, aerosols, syrups, emulsions, suspensions and solutions, pastes, ointments, gels, creams, lotions, powders or sprays, using inert, non-toxic, pharmaceutically suitable excipients or solvents. In this case, the therapeutically active compound should in each case be present in a concentration of about 0.1 to 99.9% by weight, preferably of about 0.5 to 95% by weight, of the total mixture, i.e. in amounts which are sufficient in order to achieve the given dose range.

The active compound or compounds can optionally be present in one or more of the abovementioned excipients and in microencapsulated form.

Apart from the compounds according to the invention, the abovementioned pharmaceutical preparations can also contain further pharmaceutical active compounds.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound using suitable liquid excipient materials can be employed.

In general, it has proven advantageous both in human and in veterinary medicine to administer the active compound or compounds according to the invention in total amounts of about 0.5 to about 500, preferably 5 to 100, mg/kg of bodyweight every 24 hours, if appropriate in the form of several individual doses, to achieve the desired results. An individual dose preferably contains the active compound or compounds according to the invention in amounts of about 1 to about 80, in particular 3 to 30, mg/kg of body weight.

In general, it has proven advantageous in the case of intravenous administration to administer amounts of from about 0.001 to 10 mg/kg, preferably about 0.01 to 5 mg/kg, of body weight to achieve effective results, and in the case of oral administration the dose is about 0.01 to 25 mg/kg, preferably 0.1 to 10 mg/kg of body weight.

In spite of this, it may sometimes be necessary to deviate from the amounts mentioned, namely depending on the body weight or on the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

Starting Compounds

EXAMPLE I 1,2-cis-4-Methylene-cyclopentane-1,2-dicarboxylic Acid

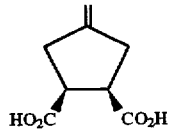

A solution of LiOH.H$_2$O (7.8 g; 185 mmol) in 150 ml of water is added dropwise at 0° C. to a solution of diethyl 1,2-cis-4-methylene-cyclopentane-1,2-dicarboxylate (19.0 g; 84 mmol) in 100 ml of THF. The resulting solution is stirred at room temperature for 20 h, the THF is stripped off in vacuo and the residue is extracted once with 40 ml of ether. The aqueous phase is brought to pH 2 with 10% strength hydrochloric acid and extracted three times with 200 ml of ethyl acetate each time. The combined ethyl acetate phases are dried over Na$_2$SO$_4$ and the solvent is stripped off in vacuo.

Yield: 13.4 g (93% of theory), M.p.: 116°–120° C., C$_8$H$_{10}$O$_4$ (170.2).

EXAMPLE II 1,2-cis-4-Methylene-cyclopentane-1,2-dicarboxylic Anhydride

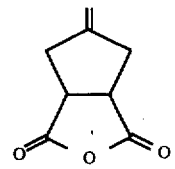

A solution of the compound from Example I (13.0 g; 76.5 mmol) in 65 ml of propionic anhydride is heated under reflux for 3 h. The solvent is stripped off at 60° C./0.5 mm Hg and the residue is distilled.

Yield: 10.0 g (86% of theory), B.p.: 130°–140° C./0.1 mm Hg, M.p.: 47°–49° C., C$_8$H$_8$O$_3$ (152.1).

EXAMPLE III

6-Methylene-cyclopentano[3,4-d]oxazine-2,4-(1H)-dione

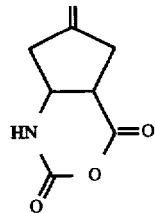

A solution of the compound from Example II (8.8 g, 58 mmol) and trimethylsilyl azide (7.9 g, 69 mmol) in 60 ml of dioxane is heated at 80° C. for 2 h. The solvent is stripped off in vacuo, the residue is taken up in 80 ml of ether and the solution is treated with H$_2$O (0.52 g, 29 mmol). The mixture is vigorously stirred for 5 min and kept at 6° C. for 2 days. Precipitated product is filtered off and washed with diethyl ether.

Yield: 4.2 g (43% of theory), M.p.: 145° C. (decomposition), C$_8$H$_9$NO$_3$ (167.2).

EXAMPLE IV

Methyl 1,2-cis-2-N-(tert-butoxycarbonyl)amino-4-(2-nitrophenyl)-selenyl-cyclopentane-1-carboxylate

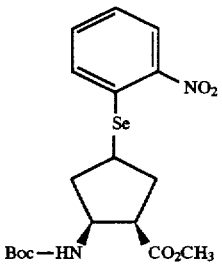

A solution of the compound from Example 63 (3.30 g, 12.7 mmol) in 50 ml of THF is treated under argon at room temperature with 2-nitrophenyl selenocyanate (3.46 g, 15.2 mmol) and then with tri-n-butylphosphine (3.08 g, 15.2 mmol). The mixture is stirred at room temperature for 1 h, the solvent is stripped off in vacuo and the residue is chromatographed on silica gel (ether: petroleum ether=2:1).

Yield: 4.45 g (79% of theory). Diastereomer ratio $D_1:D_2$= 3:1, $R_f$=0.28 and 0.39 (ether/petroleum ether=2:1), $C_{18}H_{24}N_2O_6Se$ (443.4).

General working procedure A for methyl 2-benzylaminocyclopent-1-ene-carboxylate

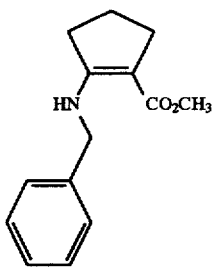

A solution of the substituted methyl 2-benzylaminocyclopent-1-ene-carboxylate (160 mmol) and benzylamine, (34.2 g, 320 mmol) in 540 ml of dichloromethane is treated with p-toluenesulphonic acid (200 mg) and 108 g of molecular sieve (4 Å) and heated under reflux in a water separator for 24 h. The mixture is filtered and the filtrate is concentrated in vacuo. The residue is chromatographed on silica gel.

EXAMPLE V

Methyl 2-Benzylamino-4,4-dimethyl-cyclopent-1-ene-carboxylate

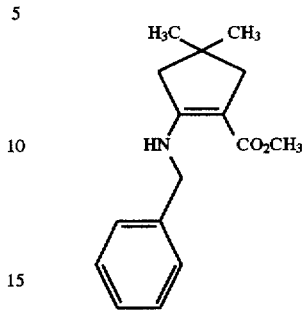

The title compound is prepared in analogy to working procedure A.

Yield: 30.0 g (72% of theory), $R_f$=0.49 (petroleum ether/ethyl acetate=3:1), $C_{16}H_{21}NO_3$ (259.3).

EXAMPLE VI

Methyl 2-Benzylamino-5-methyl-cyclopent-1-ene-carboxylate

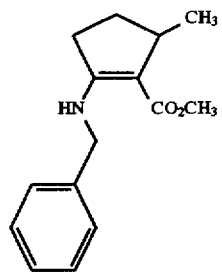

The title compound is prepared in analogy to working procedure A.

Yield: 27.9 g (71% of theory), $R_f$=0.42 (ether/petroleum ether=5:1), $C_{15}H_{19}NO_2$ (245.3).

EXAMPLE VII

Methyl 2-Benzylamino-3-methyl-cyclopent-1-ene-carboxylate

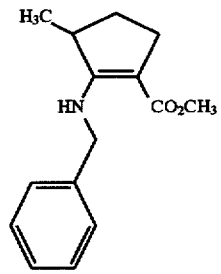

The title compound is prepared in analogy to the working procedure.

Yield: 20.0 g (51% of theory), $R_f$=0.45 (ether/petroleum ether 1:5), $C_{15}H_{19}NO_2$ (245.3).

EXAMPLE VIII

* Diethyl 4-Ethylidene-cyclopentane-1,2-dicarboxylate

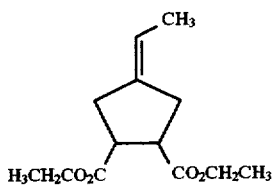

Ethyl-triphenylphosphonium bromide (100 g, 270 mmol) is added under argon at room temperature to a solution of potassium t-butoxide (24.8 g, 220 mmol) in 1 000 ml of diethyl ether and the mixture is stirred at room temperature for 20 h. A solution of diethyl 4-cyclopentanone-1,2-dicarboxylate (15.8 g, 69 mmol) in 120 ml of diethyl ether is added dropwise at 0° C. and the mixture is stirred at 0° C. for 1 h. It is treated with 300 ml of water, the organic phase is washed with saturated NaCl solution, dried over $Na_2SO_4$ and filtered, and the solvent is stripped off in vacuo. The residue is chromatographed on silica gel (petroleum ether/ether=2:1).

Yield: 13.1 g (79%) of a cis/trans diastereomer mixture, $^1$H NMR ($CDCl_3$): δ=1.23 (t, 6H); 1.58 (m, 3H), 2.3–2.6 (m, 4H), 3.0–3.22 (m, 2H), 4.17 (q, 4H), 5.35 (cm, 1H), $C_{13}H_{20}O_4$.

EXAMPLE IX

4-Ethylidene-cyclopentane-1,2-dicarboxylic Acid

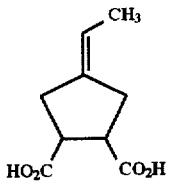

A solution of $LiOH.H_2O$ (5.1 g, 120 mmol) in 130 ml of water is added dropwise at 0° C. to a solution of the compound from Example VIII (13.1 g, 54.5 mmol) in 70 ml of THF. The solution is stirred at room temperature for 20 h, the THF is stripped off in vacuo and the residue is extracted once with 40 ml of ether. The aqueous phase is brought to pH 2 with 10% strength hydrochloric acid and extracted three times with 200 ml of ethyl acetate each time. The combined ethyl acetate phases are dried over $Na_2SO_4$ and the solvent is stripped off in vacuo.

Yield: 9.0 g (90%) of a diastereomer mixture, M.p.: 170° C., $C_9HnO_4$ (184.2).

EXAMPLE X 1,2-cis-4-Ethylidene-cyclopentane-1,2-dicarboxylic Anhydride

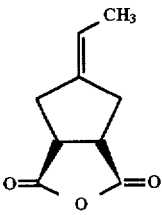

A solution of the compound from Example IX (8.25 g, 44.7 mmol) in 37 ml of propionic anhydride is heated under reflux for 3 h. The solvent is stripped off at 60° C./0.5 mm Hg and the residue is distilled.

Yield: 2.0 g (27%), M.p.: 150° C./0.1 mm Hg (bulb tube distillation), $C_9H_{18}O_2$ (166.2).

EXAMPLE XI

6-Ethylidene-cyclopentano[3,4-d]oxazine-2,4-(1H)-dione

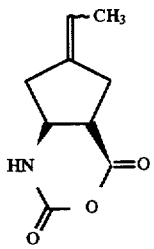

A solution of the compound from Example X (2.0 g, 12.0 mmol) and trimethylsilyl azide (1.66 g, 14.4 mmol) in 12 ml of dioxane is heated at 80° C. for 2 h. The solvent is stripped off in vacuo, the residue is taken up in 13 ml of ether and the solution is treated with water (0.22 g, 12 mmol). The mixture is vigorously stirred for 5 min and kept at 6° C. for 3 h. Precipitated product is filtered off with suction and washed with ether.

Yield: 0.48 g (22%) of a diastereomer mixture, M.p.: >250° C. (dec.), $C_9H_{11}NO_3$ (181.2).

EXAMPLE XII

Diethyl 4-Benzylidene-cyclopentane-1,2-dicarboxylate

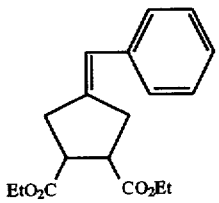

Benzyl-triphenylphosphonium chloride (95.4 g, 245 mmol) is added under argon at room temperature to a solution of potassium t-butoxide (22.0 g, 196 mmol) in 1200 ml of diethyl ether and the mixture is stirred at room temperature for 4 h. A solution of diethyl 4-cyclopentanone-1,2-dicarboxylate (14.0 g, 61.3 mmol) is then added dropwise at 0° C. and the mixture is heated under reflux for 8 d. Further working up is carried out in analogy to the procedure of Example VIII.

Yield: 15.9 g (86%), cis/trans isomers, $R_f$=0.37, 0.43 (petroleum ether/ether=5:1). $^1$H NMR (CDCl$_3$): δ=1.25 (2t, 6H), 2.70–3.35 (m, 6H), 4.17 (q, 4H), 6.38 (cm, 1H), 7.12–7.40 (m, 5H). $C_{18}H_{22}O_4$ (302.37).

EXAMPLE XIII

4-Benzylidene-cyclopentane-1,2-dicarboxylic Acid

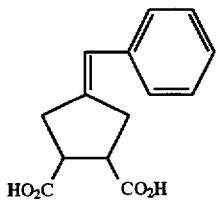

The title compound is prepared in analogy to the procedure of Example IX.

Yield: 12.8 g (100%), M.p.: 172° C., $C_{14}H_{14}O_4$ (246.26).

EXAMPLE XIV

Diethyl 1,2-cis-4-Difluoromethylene-cyclopentane-1,2-dicarboxylate

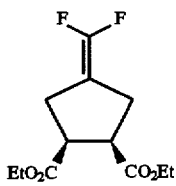

Tris-(dimethylamino)-phosphine (57.1 g, 350 mmol) is added dropwise at 0° C. under argon in the course of 30 min to a solution of diethyl 1,2-cis-4-cyclopentanone-1,2-dicarboxylate (20.0 g, 87.6 mmol) and dibromodifluoromethane (36.8 g, 175 mmol) in THF (400 ml). The mixture is slowly allowed to warm to room temperature and stirred for a further 1 h at this temperature. It is treated with triethylamine (17.6 g, 175 mmol) and stirred at room temperature for 15 h. After addition of 500 ml of water, the reaction mixture is extracted with diethyl ether (3×500 ml) and the combined organic phases are washed with satd. NaCl solution (2×300 ml), dried over Na$_2$SO$_4$ and concentrated in vacuo. The residue is chromatographed on silica gel (petroleum ether/diethyl ether=1:1).

Yield: 5.93 g (27%), $^1$H NMR (CDCl$_3$): δ=1.28 (t, 6H), 2.55–2.90 (4H), 3.17 (dt, 2H), 4.17 (q, 4H). $C_{12}H_{16}F_2O_4$ (262.4).

EXAMPLE XV 1,2-cis-4-Difluoromethylene-cyclopentane-1,2-dicarboxylic Acid

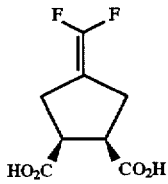

The title compound is prepared in analogy to the procedure of Example IX.

Yield: 3.86 g (85%), M.p.: 147°–149° C., $C_8H_8F_2O_4$ (206.1).

EXAMPLE XVI

4-Difluoromethylene-cyclopentane-1,2-dicarboxylic Anhydride

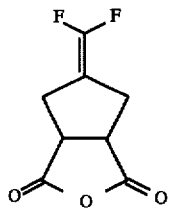

The title compound is prepared in analogy to the procedure of Example X.

Yield: 2.25 g (65%), M.p.: 140°–145° C./0.05 mbar (bulb tube distillation), $C_8H_6F_2O_3$ (188.1).

EXAMPLE XVII

6-Difluoromethylene-cyclopentano[3,4-d]oxazine-2,4-(1H)-dione

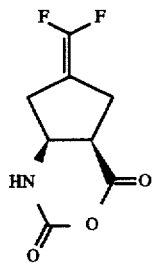

The title compound is prepared in analogy to the procedure of Example XI.

Yield: 1.40 g (59%), M.p.: 130° C. (dec.), $C_8H_7F_2NO_3$ (203.1).

EXAMPLE XVIII

Diethyl 4,4-Difluoro-cyclopentane-1,2-dicarboxylate

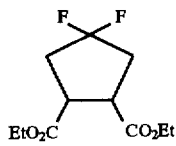

Diethylaminosulphur trifluoride (11.28 g, 70 mmol) is added dropwise at 0° C. to a solution of diethyl 4-cyclopentanone-1,2-dicarboxylate (6.43 g, 28.2 mmol) in 100 ml of toluene and the solution is stirred at room temperature for 5 d. The solution is poured into ice-water, the mixture is extracted with ethyl acetate (2×200 ml), the organic phase is dried ($Na_2SO_4$) and the solvent is stripped off in vacuo. The residue is chromatographed on silica gel (petroleum ether/diethyl ether=1:1).

Yield: 3.79 g (56% of a diastereomer mixture, $R_f$=0.65 (petroleum ether/diethyl ether=1:1), $^1$H NMR ($CDCl_3$): δ=1.28 (t, 6H), 2.52 (cm, 4H), 3.29 (cm, 2H), 4.18 (q, 4H), $C_{11}H_{16}O_4F_2$ (250.2).

EXAMPLE XIX 4,4-Difluoro-cyclopentane-1,2-dicarboxylic Acid

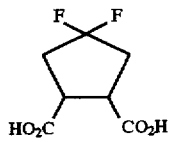

The title compound is prepared in analogy to the procedure of Example XI.

Yield: 4.40 g (77%), M.p.: 128° C., $C_7H_8O_4F_2$ (194.1).

EXAMPLE XX 4,4-Difluoro-cyclopentane-1,2-dicarboxylic Anhydride

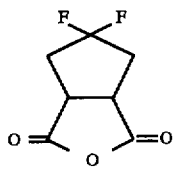

The title compound is prepared in analogy to the procedure of Example X.

Yield: 2.90 g (75%), M.p.: 150° C./0.15 mbar (bulb tube distillation), $C_7H_6F_2O_3$ (176.12).

EXAMPLE XXI 6,6-Difluoro-cyclopentano[3,4-d]oxazine-2,4-(1H)-dione

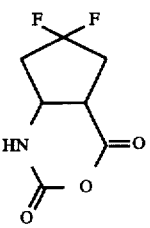

The title compound is prepared in analogy to the procedure of Example XI.

Yield: 2.33 g (74%), M.p.: 116° C. (dec.), $C_7H_7F_2NO_3$ (191.1).

EXAMPLE XXII

Ethyl 3-Benzyloxymethyl-cyclopentan-2-one-1-carboxylate

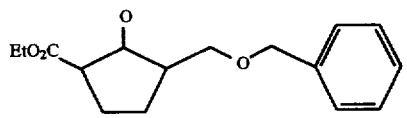

A solution of 2-benzyloxymethyl-cyclopentan-2-one (23.5 g, 115 mmol, preparation according to Murata S., Tetrahedron Letters, 1980, 2527) in 100 ml of THF is added dropwise at −78° C. under argon to a solution of lithium diisopropylamide (138 mmol) in 300 ml of THF and the mixture is stirred at −78° C. for 30 min and at −40° C. for 10 min. 1,3-Dimethyltetrahydro-2-(1H)-pyrimidone (14.7 g, 115 mmol) is added dropwise at −78° C. and the solution thus prepared is finally added dropwise at −78° C. to a solution of ethyl cyanoformate (22.8 g, 230 mmol). After 10 min, the reaction mixture is poured into 200 ml of water, the THF is stripped off in vacuo and the residue is taken up in 1100 ml of diethyl ether. The organic phase is washed with water (3×100 ml), dried ($Na_2SO_4$) and concentrated in vacuo. The residue is chromatographed on silica gel (petroelum ether/diethyl ether=2:1).

Yield: 19.3 g (61%), $R_f$=0.34 (petroleum ether/diethyl ether=2:1), $C_{16}H_{20}O_4$ (276.3).

EXAMPLE XXIII

Ethyl 2-Benzylamino-3-benzyloxymethyl-cyclopent-1-ene-1-carboxylate

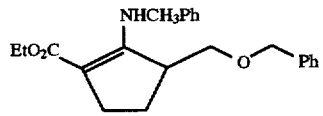

The title compound is prepared in analogy to the procedure of Example V starting from Example XXII.

Yield: 14.2 g (54%), $R_f$=0.62 (petroleum ether/diethyl ether=2:1), $C_{24}H_{27}NO_3$ (377.48).

PREPARATION EXAMPLES

Example 1

Ethyl 1,2-cis-2-Amino-4-methylene-cyclopentane-1-carboxylate Hydrochloride

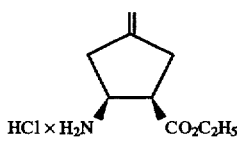

Acetyl chloride (3.01 g, 38.4 mmol) is added dropwise to a solution of the compound from Example III (3.90 g, 23.3 mmol) in 48 ml of EtOH. The solution is stirred at room temperature for 20 h and the solvent is stripped off in vacuo.

Yield: 4.79 g (100%), $R_f$=0.48 (ether:acetonitrile:conc. $NH_3$/10:1:0.1), $C_9H_{15}NO_2\times HCl$ (169.2×36.5).

Example 2

1,2-cis-2-Amino-4-methylene-cyclopentane-1-carboxylic acid Hydrochloride

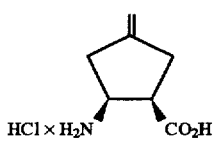

A solution of the compound from Example III (0.500 g, 3.00 mmol) in 30 ml of 0.1N HCl (3.00 mmol) is stirred at room temperature for 4 h. The solvent is stripped off in vacuo at 30° C. and the residue is dried at 30° C./0.1 mm Hg for 12 h.

Yield: 0.513 g (96%), M.p.: 190° C., $C_7H_{11}NO_3\times HCl$ (141.2×36.5).

Example 3

Ethyl 1,2-cis-2-N-(tert-butoxycarbonyl)amino-4-methylene-cyclopentane-1-carboxylate

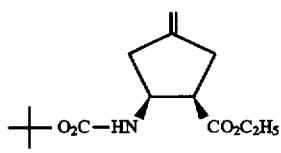

A solution of the compound from Example 1 (15.4 g, 75.0 mmol) and triethylamine (22.8 g, 225 mmol) in 225 ml of $CH_2Cl_2$ is treated at 0° C. with di-tert-butyl dicarbonate (24.8 g, 112 mmol) and the mixture is stirred at room temperature for 4 h. The solvent is stripped off in vacuo and the residue is chromatographed on silica gel (ether/petroleum ether=1:3).

Yield: 18.0 g (91%)

$R_f$=0.29 (ether/petroleum ether=1:3)

$C_{14}H_{23}NO_4$ (269.3)

Example 4

Ethyl 1,2-cis-3-N-(tert-butoxycarbonyl)amino-4-oxo-cyclopentane-1-carboxylate

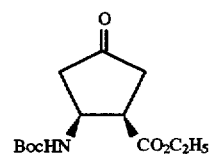

Ozone is passed through a solution of the compound from Example 3 (18.0 g, 67.0 mmol) at −70° C. until the solution is coloured blue and oxygen is then passed through until it is decolorised. The mixture is treated with dimethyl sulphide (24.8 g; 0.40 mol), allowed to warm to room temperature and stirred at this temperature for a further 2 h. The solvent is stripped off in vacuo, the residue is stirred with diisopropyl ether, and the solid is filtered off with suction and washed with diethyl ether.

Yield: 15.1 g (83%)

M.p.: 132° C.

$C_{13}H_{21}NO_5$ (271.3)

Example 5

Ethyl 1,2-cis-2-amino-4-oxo-cyclopentane-1-carboxylate hydrochloride

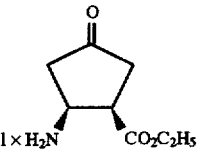

A solution of the compound from Example 4 (0.980 g, 3.60 mmol) in 5 ml of 4N HCl in dioxane is stirred at room temperature for 3 h. The solvent is stripped off in vacuo and the residue is dried at 50° C./0.1 mm Hg for 20 h.

Yield: 0.734 g (98%) $^1$H NMR (DMSO-$d_6$): δ=1.24 (t, J=7 Hz, 3H); 2.14–2.80 (m, 4H); 3.49–3.62 (m, 1H), 4.02–4.28 (m, 3H); 8.53 (s, broad, 3H).

$C_8H_{13}NO_3\times HCl$ (171.2×36.5)

Example 6

1,2-cis-2-Amino-4-oxo-cyclopentane-1-carboxylic acid hydrochloride

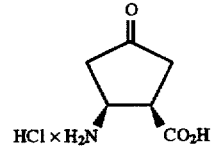

A solution of the compound from Example 5 (0.500 g, 2.41 mmol) in 40 ml of 3N HCl is heated at 80° C. for 2 h. The solvent is stripped off in vacuo and the residue is dried at 50° C./0.1 mm Hg for 20 h.

Yield: 0.432 g (100%)

$^1$H NMR (DMSO-$d_6$) δ=2.42–2.76 (m, 4H); 3.42–3.56 (m, 1H); 4.08 (s, broad, 1H), 8.45 (s, broad, 3H). $C_6H_9NO_3\times HCl$ (141.3×36.5)

Example 7

Ethyl 1,2-cis-2-N-(tert-butoxycarbonyl)amino-4-hydroxy-cyclopentane-carboxylate

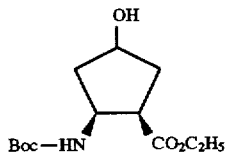

A solution of the compound from Example 6 (5.00 g, 18.5 mmol) in 150 ml of MeOH is treated at 5° C. with NaBH$_4$ (0.345 g, 9.0 mmol) and stirred at room temperature for 1 h. The solvent is stripped off in vacuo, the residue is taken up in water and the solution is extracted with CH$_2$Cl$_2$. The organic phase is dried over Na$_2$SO$_4$ and the solvent is stripped off in vacuo.

Yield: 4.9 g (97%)

Diastereomer ratio D$_1$:D$_2$=3:1

R$_f$=0.42 and 0.48 (ether)

C$_{13}$H$_{23}$NO$_5$ (273.3)

Example 8

Ethyl 1,2-cis-2-amino-4-hydroxy-cyclopentanecarboxylate hydrochloride

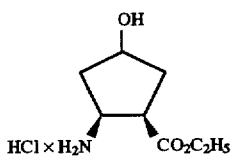

A solution of the compound from Example 7 (1.10 g, 4.0 mmol) in 6 ml of 4N HCl in dioxane is stirred at room temperature for 1 h. The solvent is stripped off in vacuo and the residue is dried at 50° C./0.1 mm Hg for 20 h.

Yield: 0.82 g (97%)

Diastereomer ratio D$_1$:D$_2$=3:1

MS (DEI): m/e=174 (M+H)

C$_8$H$_{15}$NO$_3$×HCl (173.2×36.5)

Example 9

1,2-cis-2-Amino-4-hydroxy-cyclopentane-1-carboxylic acid hydrochloride

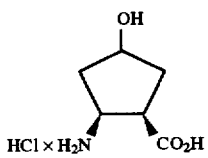

A solution of the compound from Example 8 (210 mg, 1.0 mmol) in 13 ml of 3N HCl is stirred at 80° C. for 2 h. The solvent is stripped off in vacuo and the residue is dried at 50° C./0.1 mm Hg for 20 h.

Yield: 151 mg (83%)

Diastereomer ratio D$_1$:D$_2$=3:1

MS (DEI): m/e=146 (M+H)

C$_6$H$_{11}$NO$_3$×HCl (145.2×36.5)

Example 10

Methyl 1,2-cis-2-benzylamino-4,4-dimethyl-cyclopentane-1-carboxylate

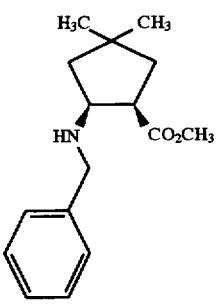

A solution of the compound from Example VI (8.15 mmol) in 70 ml of EtOH is treated with 1 g of platinum (5% on active carbon) and hydrogenated at 35° C. and 80 bar of H$_2$ for 20 h. The catalyst is filtered off, the filtrate is concentrated in vacuo and the residue is chromatographed on silica gel.

Yield: 2.13 g (51%)

R$_f$=0.49 (ethyl acetate/petroleum ether=1:2)

C$_{16}$H$_{23}$NO$_2$ (261.3)

Example 11

Methyl 1,2-cis-2-benzylamino-5-methyl-cyclopentane-1-carboxylate

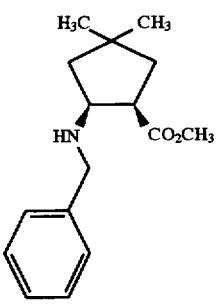

The title compound is prepared in analogy to the procedure of Example 10.

Yield: diastereomer D$_1$: 0.67 g (33%)

R$_f$=0.49 (ethyl acetate/petroleum ether=1:2)

Diastereomer D$_2$=0.59 (29%)

R$_f$=0.34 (ethyl acetate/petroleum ether=1:2)

C$_{15}$H$_{21}$NO$_2$ (247.34)

Example 12

Methyl 1,2-cis-2-benzylamino-3-methyl-cyclopentane-1-carboxylate

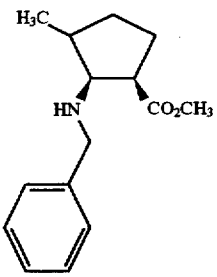

The title compound is prepared in analogy to the procedure of Example 10.

Yield: 1.41 g (71%)

2 diastereomers $D_1:D_2=4:1$ $R_f=0.49$ and 0.31 (ethyl acetate/petroleum ether=1:4)

$C_{15}H_{21}NO_2$ (247.34)

Example 13

Methyl 1,2-cis-2-amino-4,4-dimethyl-cyclopentane-1-carboxylate hydrochloride

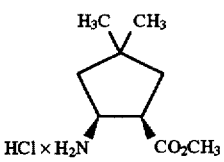

A solution of the compound from Example 10 (7.70 mmol) in 77 ml of 0.1N HCl (7.70 mmol), 80 ml of $H_2O$ and 110 ml of EtOH is treated with 710 mg of palladium (10% on active carbon) and hydrogenated at room temperature and 3 bar of $H_2$ for 20 h. The catalyst is filtered off, the filtrate is concentrated in vacuo and the residue is dried at 50° C./0.1 mm Hg for 12 h.

Yield: 1.52 g (95%)

M.p.: 148° C.

$C_9H_{17}NO_2 \times HCl$ (171.2×36.5)

Example 14

Methyl 1,2-cis-2-amino-5-methyl-cyclopentane-1-carboxylate hydrochloride

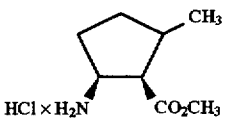

The title compound is obtained in analogy to the procedure of Example 10.

Yield: diastereomer A: 1.43 g (96%)

M.p.: 169° C.

Diastereomer B: 1.46 g (98%)

M.p.: 64° C.

$C_8H_{15}NO_2 \times HCl$ (157.2×36.5)

Example 15

Methyl 1,2-cis -2-amino-3-methyl-cyclopentane-1-carboxylate hydrochloride

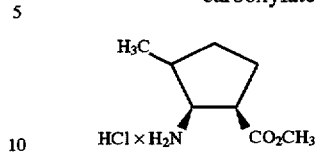

The title compound is obtained in analogy to the procedure of Example 10.

Yield: 1.50 g (100%)

2 diastereomers: $D_1:D_2=4:1$ $R_f=0.45$ (ether/acetonitrile/conc. $NH_3=10:1:0.1$)

$C_8H_{15}NO_2 \times HCl$ (157.2×36.5)

Example 16

1,2-cis-2-Amino-4,4-dimethyl-cyclopentane-1-carboxylic acid hydrochloride

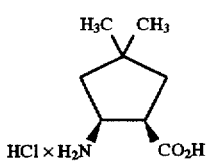

A solution of the compound from Example 13 (4.20 mmol) in 70 ml of 3N HCl is heated under reflux for 2 h. The solvent is stripped off in vacuo, and the residue is washed with THF and dried at 50° C./0.1 mm Hg for 20 h.

Yield: 0.81 g (100%)

M.p.: 190° C. (dec.)

$C_8H_{15}NO_2 \times HCl$ (157.2×36.5)

Examples 17a and 17b 1,2-cis-2-Amino-5-methyl-cyclopentane-1-carboxylic acid hydrochloride

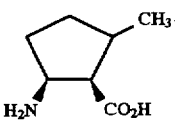

The title compound is prepared in analogy to the procedure of Example 16.

Yield: diastereomer A: 0.61 (81%) (Example 17a)

M.p.: 134° C.

Diastereomer B: 0.73 g (97%) (Example 17b)

M.p.: 200° C. (dec.)

$C_7H_{13}NO_2 \times HCl$ (143.2×36.5)

Example 18

1,2-cis-2-Amino-3-methyl-cyclopentane-1-carboxylic acid hydrochloride

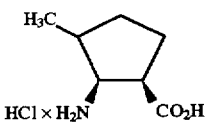

The title compound is prepared in analogy to the procedure of Example 16.

Yield: 0.68 g (90%)

Diastereomer ratio $D_1:D_2=4:1$

M.p.: 206° C.

$C_7H_{13}NO_2 \times HCl$ (143.2×36.5)

Example 19

1,2-cis-2-Amino-2-methyl-cyclopentane-1-carboxylic acid hydrochloride

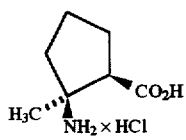

15 g (0.12 mol) of 2-methyl-6-azabicyclo[3.2.0]heptan-7-one [cf. T. Sasaki et al., Tetrahedron 32, 437 (1976)] are suspended in portions in 100 ml of concentrated hydrochloric acid, and the suspension is stirred up to the clear point at 40° C. The solution is extracted once with diethyl ether and the aqueous phase is concentrated to dryness. After drying in a high vacuum, 20.7 g (96%) of a white solid are obtained.

M.p.: 194° C.

$C_7H_{13}NO_2 \times HCl$ (143×36.5)

Example 20

1,2-cis-2-Amino-4-methyl-cyclopentane-1-carboxylic acid

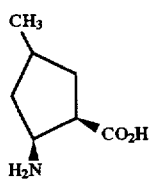

3 g (0.024 mol) of 4-methyl-6-azabicyclo[3.2.0]heptan-7-one [preparation: T. Sasaki et al., Tetrahedron 32, (1976)] are stirred at room temperature for 2 h together with 15 ml of conc. hydrochloric acid. After extracting the solution with ether, the extract is concentrated to dryness. The residue is dried in a high vacuum at 40° C.

Yield: 2.9 g (67%)

M.p.: 188.5° C.

$C_7H_{13}NO_2 \times HCl$ (143×36.5)

Example 21

1,2-cis-2-N-(9-Fluorenylmethoxycarbonyl)amino-4-methylene-cyclopentane-1-carboxylic acid

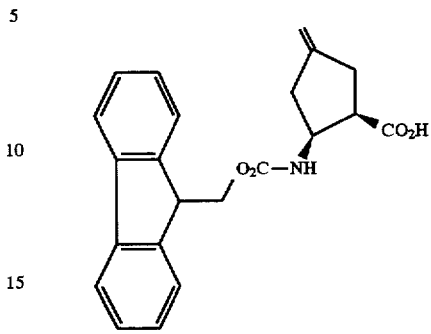

A solution of N-(9-fluorenylmethoxycarbonyloxy)-succinimide (0.995 g, 2.95 mmol) in 10 ml of dioxane is added dropwise at 0° C. to a solution of Example 2 (0.500 g, 2.81 mmol) in 20 ml of 10% strength aqueous $N_2CO_3$ solution. The mixture is stirred at room temperature for 12 h and extracted three times with 10 ml of ether each time. The aqueous phase is adjusted to pH 2 with conc. hydrochloric acid at 0° C. and extracted twice with 40 ml of ether each time. The ether phases are dried over $Na_2SO_4$ and the solvent is stripped off in vacuo.

Yield: 0.940 g (92%)

M.p.: 137° C.

$C_{22}H_{21}NO_4$ (363.4)

Example 22 and Example 23

1,2-cis-2-N-(9-Fluorenylmethoxycarbonyl)amino-4-methyl-cyclopent-3-ene-1-carboxylic acid (Example 22)

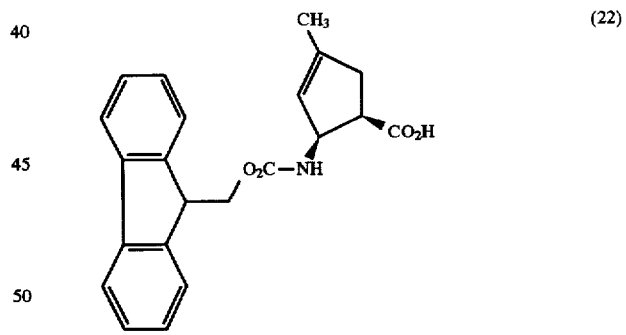

(22)

1,2-cis-2-N-(9-Fluorenylmethoxycarbonyl)amino-4-methyl-cyclopent-4-ene-1-carboxylic acid (Example 23)

(23)

A solution of the compound from Example 2 (0.870 g, 4.90 mmol) in 20 ml of 10% strength hydrochloric acid is stirred at room temperature for 20 h and then evaporated in vacuo. The residue is dissolved in 25 ml of 10% strength $Na_2CO_3$ solution and treated at 0° C. with a solution of N-(9-fluorenylmethoxycarbonyloxy)-succinimide (1.65 g, 4.30 mmol) in 15 ml of dioxane. The mixture is stirred at room temperature for 48 h, 50 ml of $H_2O$ are added and it is extracted twice with 20 ml of ether each time. The aqueous phase is adjusted to pH 2 at 0° C. and extracted twice with 50 ml of ether each time. The ether phases are dried over $Na_2SO_4$, the solvent is stripped off in vacuo and the residue is chromatographed on silica gel (methylene chloride/methanol 20:1).

Yield: 0.211 g (12%) (Example 22)

$R_f$=0.31 (methylene chloride/methanol 20:1) (Example 22)

Yield: 0.187 g (11%) (Example 23)

$R_f$=0.28 (methylene chloride/methanol=20:1) (Example-23)

$C_{22}H_{21}NO_4$ (363.4)

Example 24

1,2-cis-2-Amino-4-methyl-cyclopent-4-ene-1-carboxylic acid

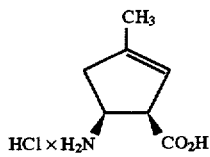

A solution of Example 2 (0.870 g, 4.90 mmol) in 20 ml of 10% strength hydrochloric acid is stirred at room temperature for 20 h and then evaporated in vacuo. The residue is dissolved in 8 ml of ethanol, treated with 15 ml of ether and allowed to stand at 5° C. for 5 d. Precipitated product is filtered off with suction and washed with ether.

Yield: 0.246 g (28%)

M.p.: 196° C.

$C_7H_{11}NO_2 \times HCl$ (141.2×36.5)

Example 25

1,2-cis -2-Amino -4-methyl-cyclopent-4-ene-1-carboxylic acid

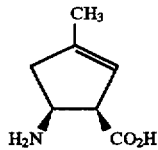

A solution of Example 23 (0.380 g, 1.05 mmol) in 30 ml of liquid ammonia is stirred for 10 h. The ammonia is allowed to evaporate, the residue is treated with 50 ml of ether, the mixture is stirred at room temperature for 1 h and filtered, and the residue is washed with 20 ml of ether. The residue is taken up in 5 ml of water and the mixture is stirred for 10 min. It is filtered, the solid is washed with 3 ml of water and the filtrate is concentrated in vacuo. The residue is recrystallised from 80% strength aqueous ethanol.

Yield: 0.082 g (55%)

M.p.: 190° C.

$C_7H_{11}NO_2$ (141.2)

Example 26

1,2-cis-2-Amino-4-methyl-cyclopent-3-ene-1-carboxylic acid

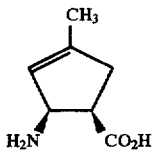

A solution of Example 22 (0.410 g, 1.13 mmol) in 30 ml of liquid ammonia is stirred for 10 h. The ammonia is allowed to evaporate, the residue is treated with 50 ml of ether, the mixture is stirred at room temperature for 1 h and filtered and the residue is washed with 20 ml of ether. The residue is taken up in 5 ml of water and the mixture is stirred for 10 min. It is filtered, the solid is washed with 3 ml of water and the filtrate is concentrated in vacuo. The residue is recrystallised from 80% aqueous ethanol.

Yield: 0.112 g (70%)

M.p.: 221° C.

$C_7H_{11}NO_2$ (141.2)

Example 27

1,2-cis -2-Amino-4-methyl-cyclopent-3-ene-1-carboxylic acid hydrochloride

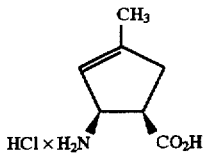

The compound from Example 2 (0.110 g, 0.78 mmol) is dissolved in 7.80 ml (0.78 mmol) of 0.1N HCl. The solution is then evaporated in vacuo.

Yield: 0.138 g (100%)

M.p.: 188° C. (dec.)

$C_7H_{11}NO_2 \times HCl$ (141.2×36.5)

Example 28

(R)-Phenethylammonium (+)-1,2-cis-2-(9-fluorenylmethoxy-carbonyl)amino-4-methylene-cyclopentane-1-carboxylate

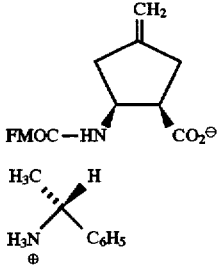

A solution of Example 21 (10.0 g, 27.5 mmol) in 4.5 ml of tert-butyl methyl ether and 15 ml of EtOH is treated with (R)-(+)-phenethylamine (3.33 g, 27.5 mmol). The mixture is heated under reflux and about 80 ml of EtOH are added

Example 29

(S)-Phenethylammonium (−)-1,2-cis-2-(9-fluorenylmethoxy-carbonyl)amino-4-methylene-cyclopentane-1-carboxylate

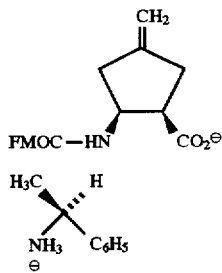

The preparation takes place analogously as described in Example 28 using (S)-phenethylamine instead of (R)-phenethylamine.

Yield: 3.48 g (26%)

M.p.: 165° C.

$[\alpha]_D^{20} = 17.8°$ (c=0 73, MeOH)

$C_{20}H_{21}NO_4 \times C_8H_{11}N$ (363.4×121.2)

Example 30

(−)-1,2-cis-2-(9-Fluorenylmethoxycarbonyl)amino-4-methylene-cyclopentane-1-carboxylic acid

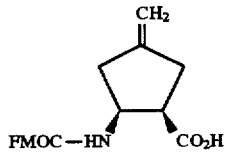

Example 29 (3.49 g, 7.20 mmol) is suspended in 40 ml of water and 40 ml of ethyl acetate. The mixture is treated with 1N HCl to pH 2, the phases are separated and the aqueous phase is extracted a further 2 x with 40 ml of ethyl acetate each time. The combined organic phases are dried over $Na_2SO_4$ and the solvent is stripped off in vacuo.

Yield: 2.46 g (94%)

$[\alpha]_D^{20} = -18.8°$ (c=1, MeOH)

M.p.: 137° C.

Enantiomer excess e.e.=99.5% (HPLC, Chiralpak AS)

$C_{22}H_{21}NO_4$ (363.4)

Example 31

(+)-1,2-cis-2-(9-Fluorenylmethoxycarbonyl)amino-4-methylene-cyclopentane-1-carboxylic acid

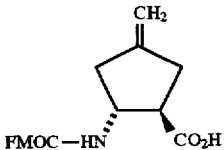

The preparation is carried out as for Example 30.

Yield: 2.46 g (94%)

$[\alpha]_D^{20} = +18.4°$ (c=0.48, MeOH)

M.p.: 137° C.

Enantiomer excess e.e.=99.0% (HPLC, Chiralpak AS)

$C_{22}H_{21}NO_4$ (363.4)

Example 32

(−)-1,2-cis-2-Amino-4-methylene-cyclopentane-1-carboxylic acid hydrochloride

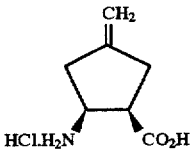

Example 31 (1.35 g, 3.71 mmol) is treated with 100 ml of liquid ammonia, the mixture is stirred for about 10 h and the ammonia is then evaporated. The residue is treated with 120 ml of ether, and the mixture is stirred at room temperature for 1 h. It is filtered and the residue is taken up in 5 ml of water, the mixture is filtered again, the residue is washed with 3 ml of water and the filtrate is concentrated in vacuo. The residue is recrystallised from 80% strength aqueous ethanol. The free amino acid obtained (0.451 g, 3.19 mmol) is treated with 1N HCl (31.9 ml, 3.19 mmol) and the resulting solution is concentrated in vacuo and the residue is dried in vacuo at 50° C./0.1 mm Hg.

Yield: 0.567 g (86%)

M.p.: 184° C., $[\alpha]_D^{20} = -11.6°$ (c=1, $H_2O$)

$C_7H_{11}NO_2 \times HCl$ (141.2×36.5)

Example 33

(+)-1,2-cis -2-Amino-4-methylene-cyclopentane-1-carboxylic acid hydrochloride

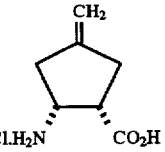

The preparation is carried out analogously, as described for Example 32.

Yield: 0. 566 g (86%)

M.p.: 186° C.

$[\alpha]_D^{20} = +11.4°$ (c=1.04, H$_2$O)

C$_7$H$_{11}$NO$_2$×HCl (141.2×36.5)

Example 34

1,2-cis-2-Amino-4-ethylidene-cyclopentane-1-carboxylic acid hydrochloride

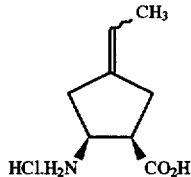

The compound from Example XI (0.30 g, 1.66 mmol) is treated with 0.1N HCl (16.6 mmol, 1.66 mmol). The mixture is stirred for 5 h until a clear solution has formed. The solvent is stripped off in vacuo at 30° C. and the residue is dried at 30° C./0.1 mm Hg for 12 h.

Yield: 0.32 g (100%) of a diastereomer mixture

M.p.: 188° C.

C$_8$H$_{13}$NO$_2$×HCl (155.2×36.5)

Example 35

(−)-1,2-cis-2-(t-Butoxycarbonyl)amino-4-methylene-1-carboxylic acid

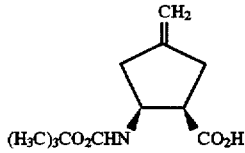

A solution of the compound from Example 32 (2.0 g, 11.3 mmol) in 20 ml of dioxane is treated with 16.8 ml of a 1M Na$_2$CO$_3$ solution and, at 0° C., with di-tert-butyl dicarbonate (2.68 g, 12.3 mmol). The mixture is stirred at room temperature for 20 h. 30 ml of ethyl acetate are added and the solution is brought to pH 2 with 10% strength hydrochloric acid. The aqueous phase is extracted twice more with 30 ml of ethyl acetate each time. The combined organic phases are washed with satd. NaCl solution, dried over Na$_2$SO$_4$ and concentrated in vacuo.

Yield: 2.73 g (100%)

$[\alpha]_D^{20} = -41.3°$ (c=0.72, CH$_3$OH)

C$_{12}$H$_{19}$NO$_4$ (241.3)

Example 36

Ethyl (−)-1,2-cis-2-(tert-butoxycarbonyl)amino-4-methylene-cyclopentane-1-carboxylate

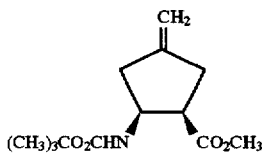

A solution of dicyclohexylcarbodiimide (2.57 g, 12.5 mmol) in 10 ml of dichloromethane is added dropwise at 0° C. to a solution of the compound from Example 35 (2.73 g, 11.3 mmol), 4-dimethylaminopyridine (0.14 g, 1.1 mmol) and methanol (1.09 g, 34 mmol) in 30 ml of dichloromethane. The mixture is stirred at room temperature for 2 h; and precipitated dicyclohexylurea is filtered off with suction and washed with 50 ml of dichloromethane. The filtrate is washed with 30 ml of 0.1N HCl and 30 ml of satd. NaHCO$_3$ solution, dried over Na$_2$SO$_4$ and concentrated in vacuo. The residue is chromatographed on silica gel (petroleum ether/ethyl acetate=3:1).

Yield: 2.36 g (82%)

M.p.: 64° C.

$[\alpha]_D^{20} = -86.8°$ (c=1.02, CH$_3$OH)

C$_{13}$H$_{21}$NO$_4$

Example 37

Methyl (−)-1,2-cis-2-amino-4-methylene-cyclopentane-1-carboxylate hydrochloride

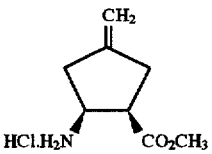

(tert-Butyldimethyl)silyl trifluoromethanesulphonate (3.27 g, 12.3 mmol) is added dropwise at room temperature under argon to a solution of the compound from Example 36 (2.10 g, 8.20 mmol) and 2,6-lutidine (1.76 g, 16.5 mmol) in 50 ml of dichloromethane. The mixture is stirred for 15 min, treated with 100 ml of satd. NH$_4$Cl solution and extracted twice with 100 ml of ether each time. The organic phases are washed with satd. NaCl solution, dried over MgSO$_4$ and concentrated in vacuo. The residue is dissolved in 50 ml of THF and treated at 0° C. with water (0.30 g, 16.5 mmol) and tetrabutylammonium fluoride (1.1M solution in THF, 7.5 ml, 8.2 mmol). The mixture is stirred at 0° C. for 1 h, 100 ml of water are added, the solution is brought to pH 9 with conc. NH$_3$, 15 g of NaCl are added and the mixture is extracted three times with 80 ml of ethyl acetate each time. The organic phases are dried over MgSO$_4$ and concentrated in vacuo. The residue is chromatographed on silica gel (ether/acetonitrile/conc.

NH$_3$=10:1:0.1).

Yield: 1.15 g (73%)

M.p.: 146° C./$[\alpha]_D^{20} = -4.2°$ (c=1.23, H$_2$O)

C$_8$H$_{13}$NO$_2$×HCl (155.2×36.5)

Example 38

Methyl (−)-1,2-cis-2-(N-tert-butoxycarbonyl)-glycinyl)-amino-4-methylene-cyclopentane-1-carboxylate

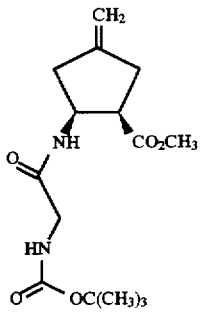

A solution of dicyclohexylcarbodiimide (0.430 g, 2.09 mmol) in 2 ml of THF is added dropwise under argon at 0° C. to a solution of the compound from Example 36 (0.40 g, 2.09 mmol), 1-hydroxy-1H-benzotriazole×H$_2$O (0.282 g, 2.09 mmol), N-ethylmorpholine (0.261 g, 2.09 mmol) and N-(tert-butoxycarbonyl)glycine (0.366 g, 2.09 mmol) in 18 ml of THF. The mixture is stirred at 0° C. for 1 h and at room temperature for 20 h and filtered, the solid is washed with 10 ml of THF and the filtrate is concentrated in vacuo. The residue is dissolved in 40 ml of ethyl acetate, washed with 20 ml of satd. NaHCO$_3$ solution and 20 ml of satd. NaCl solution, dried over Na$_2$SO$_4$ and concentrated in vacuo.

Yield: 0.585 g (100%)

$^1$H NMR (d$_6$-DMSO): α=1.38 (s, 5H); 2.18–2.73 (m, 4H); 3.08 (dt, 1H); 3.18 and 3.46 (AB of ABX, 2H); 3.57 (s, 3H); 4.40 (ddt, 1H); 4.90 (m, 2H); 6.88 (X of ABX, 1H), 7.71 (d, 1H)

C$_{15}$H$_{24}$N$_2$O$_5$ (312.4)

Example 39

Methyl (−)-1,2-cis-2-(N-tert-butoxycarbonyl(S)-alanyl)-amino-4-methylene-cyclopentane-1-carboxylate

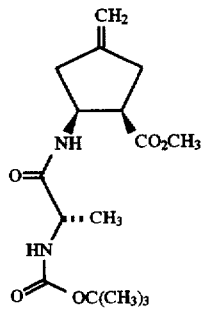

The title compound is prepared in analogy to the procedure of Example 38.

Yield: 0.630 g (86%)

$^1$H NMR (d$_6$-DMSO): α=1.09 (d, 3H), 1.36 (s, 9H), 2.22–2.72 (m, 4H), 3.10 (dt, 1H), 3.52 (s, 3H), 3.95 (dq, 1H), 4.40 (ddt, 1H), 4.90 (cm, 2H), 6.78 (d, 1H) 7.83 (d, 1H).

C$_{16}$H$_{26}$N$_2$O$_5$ (326.4)

Example 40

Methyl (−)-1,2-cis-2-(N-glycinyl)amino-4-methylene-cyclopentane-1-carboxylate hydrochloride

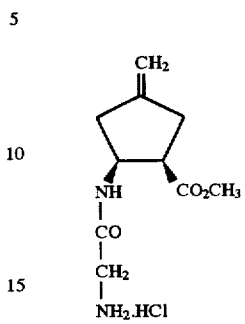

(tert-Butyldimethyl)silyl trifluoromethanesulphonate (1.10 g, 4.15 mmol) is added dropwise at 0° C. under argon to a solution of the compound from Example 38 (0.52 g, 1.66 mmol) and 2,6-lutidine (0.59 g, 5.50 mmol) in 10 ml of dichloromethane and the mixture is stirred at room temperature for 20 h. It is treated with 20 ml of satd. NH$_4$Cl solution, extracted twice with 50 ml of ether each time, the organic phase is washed with saturated NaCl solution and dried over MgSO$_4$ and the solvent is stripped off in vacuo.

The residue is taken up in 10 ml of THF, the mixture is treated with water (0.06 g, 3.3 mmol) and a 1.1M solution of tetrabutylammonium fluoride in THF (3.0 ml, 3.3 mmol) is added dropwise at 0° C. The mixture is stirred at 0° C. for 1 h and treated with 20 ml of water, and the solution is brought to pH 9 with conc. NH$_3$. 4 g of NaCl are added, the mixture is extracted three times with 20 ml of ethyl acetate each time, and the organic phases are washed with satd. NaCl solution, dried over MgSO$_4$ and concentrated in vacuo. The residue is chromatographed on silica gel (ethyl acetate/MeOH/conc. NH$_3$=10:0.1). The free base thus obtained is taken up in 10 ml of 0.1N HCl and the solvent is stripped off in vacuo. The residue is dried at 30° C./0.1 mm Hg for 12 h.

Yield: 0.202 g (49%)

$^1$H NMR (DMSO): α=2.25–2.72 (m, 4H), 3.12 (dt, 1H), 3.40–3.62 (m, 2H), 3.59 (s, 3H), 4.49 (ddt, 1H), 4.92 (cm, 2H), 8.05 (s, broad, 3H), 8.42 (d, 1H).

C$_{10}$H$_{16}$N$_2$O$_3$×HCl (212.2×36.5).

Example 41

Methyl (−)-1,2-cis-2-(N-(S)-alanyl)amino-4-methylene-cyclopentane-1-carboxylate hydrochloride

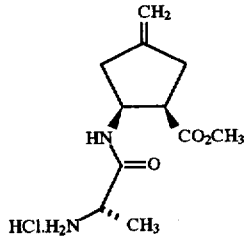

The title compound is prepared in analogy to the procedure of Example 40.

Yield: 0.249 g (57%)

$[α]_D^{20} = -66.3°$ (c=1.1 $H_2O$)

$C_{11}H_{18}N_2O_3 \times HCl$

Example 42

(−)-1,2-cis-2-[N-(9-Fluorenylmethoxycarbonyl)-(S)-norvalinyl]amino-4-methylene-cyclopentane-1-carboxylic acid

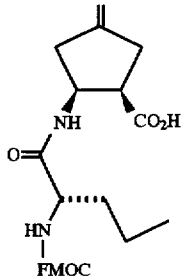

A solution of FMOC-norvaline-O-succinimide (7.38 g, 16.9 mmol) in dimethoxyethane (72 ml) is added dropwise to a solution of the compound from Example 32 (3.00 g, 16.9 mmol) and $NaHCO_3$ (2.84 g, 33.8 mmol) in 60 ml of water and the mixture is stirred overnight at room temperature. It is treated with THF (180 ml) and the solution is brought to pH 2 with 10% strength hydrochloric acid. It is extracted with ether (3×300 ml), and the combined ether phases are washed with water (100 ml) and satd. NaCl solution (100 ml) and dried over $Na_2SO_4$. The solvent is stripped off in vacuo and the residue is chromatographed on silica gel (dichloromethane/methanol=10:1).

Yield: 4.58 (59%)

M.p.: 124° C.

$R_f$=0.43 ($CH_2Cl_2$/MeOH=10:1)

$C_{27}H_{30}N_2O_5$ (462.54).

Example 43

(−)-1,2-cis-2-[N-(9-Fluorenylmethoxycarbonyl)-(S-)norleucyl]amino-4-methylene-cyclopentane-1-carboxylic acid

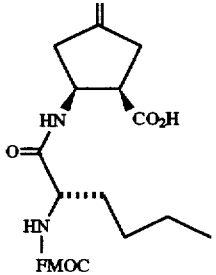

The title compound is prepared in analogy to the procedure of Example 42.

Yield: 4.97 g (74%)

M.p.: 151° C.

$F_f$=0.45 ($CH_2Cl_2$/MeOH=10.1)

$C_{28}H_{32}N_2O_5$ (476.57).

Example 44

(−)-1,2-cis-2-[N-(9-Fluorenylmethoxycarbonyl)-(S)-leucyl]amino-4-methylene-cyclopentane-1-carboxylic acid

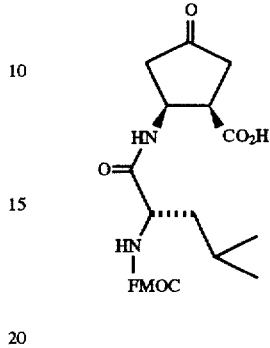

The title compound is prepared in analogy to the procedure of Example 42.

Yield: 3.17 g (47%)

$[α]_D^{20} = -28.3°$ (c=1.24, MeOH)

$R_f$=0.21 ($CH_2Cl_2$/MeOH=20:1)

$C_{28}H_{32}N_2O_5$ (476.57).

Example 45

(−)-1,2-cis-2-(N-(S)-Norvalinyl)amino-4-methylene-cyclopentane-1-carboxylic acid hydrochloride

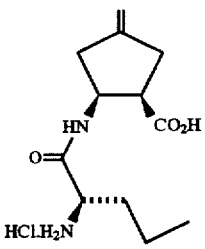

Example 42 (4.53 g, 9.80 mmol) is treated with 150 ml of liquid ammonia and stirred for about 10 h, and the ammonia is then evaporated. The residue is treated with 200 ml of ether and the mixture is stirred at room temperature for 1 h. It is filtered and the residue is taken up in 60 ml of water, the mixture is filtered again, the residue is washed with 20 ml of water and the filtrate is concentrated in vacuo. The residue is dissolved in 89 ml of 0.1N hydrochloric acid, the solvent is stripped off in vacuo and the residue is dried in vacuo over $P_2O_5$.

Yield: 2.50 g (92%)

M.p.: 130°–135° C.

$[α]_D^{20} = -27.1$ (c=1.05, MeOH)

$C_{12}H_{20}N_2O_3 \times HCl$ (240.3×36.5).

Example 46

(−)-1,2-cis -2-(N-(S)-Norleucyl)amino-4-methylene-cyclopentane-1-carboxylic acid hydrochloride

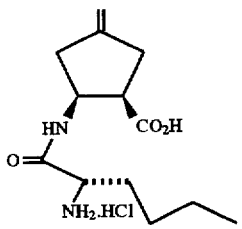

The title compound is prepared in analogy to the procedure of Example 45.

Yield: 1.63 g (54%)
M.p.: 108° C.
$[\alpha]_D^{20}=-34.3°$ (C=1.27, MeOH)
$C_{13}H_{22}N_2O_3 \times HCl$ (254.3×36.5).

Example 47

(−)-1,2-cis-2-(N-(S)-Leucyl)amino-4-methylene-cyclopentane-1-carboxylic acid hydrochloride

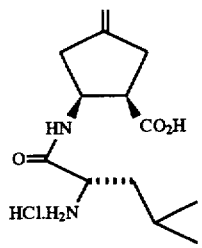

The title compound is prepared in analogy to the procedure of Example 45.

Yield: 1.82 g (96%)
M.p.: 70°–80° C.
$[\alpha]_D^{20}=-21.5°$ (C=1.4, MeOH)
$C_{13}H_{22}N_2O_3 \times HCl$ (254.3×36.5).

Example 48

Methyl (−)-1,2-cis-2-(N-butoxycarbonyl)-(S)-leucyl) amino-4-methylene-cyclopentane-1-carboxylate

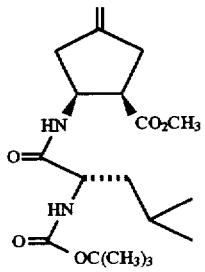

The title compound is prepared in analogy to the procedure of Example 38.

Yield: 0.584 g (56%)
M.p.: 124° C.

$C_{18}H_{30}N_2O_5$ (354.5).

Example 49

Methyl (−)-1,2-cis-2-(N-(S)-leucyl)amino-4-methylene-cyclopentane-1-carboxylate hydrochloride

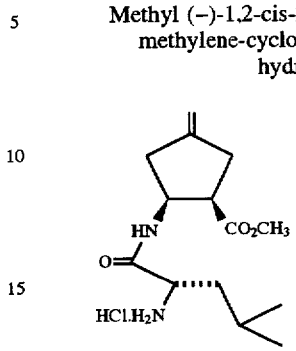

The title compound is prepared in analogy to the procedure of Example 40.

Yield: 0.259 g (65%)
M.p.: 70° C.
$[\alpha]_D^{20}-52.1°$ (c−1.04, $H_2O$).
$C_{14}H_{24}N_2O_3 \times HCl$ (268.4×36.5).

Example 50

1,2-cis-2-Amino-4-benzylidene-cyclopentane-1-carboxylic acid hydrochloride

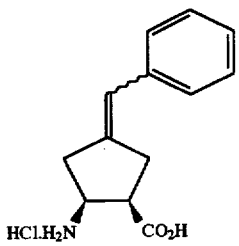

A solution of the compound from Example XIII (12.53 g, 50.9 mmol) in 43 ml of propionic anhydride is heated under reflux for 3 h. The solvent is stripped off at 60° C./0.5 mm Hg, and the residue is dried at 100° C./0.1 mm Hg for 30 min and dissolved in 60 ml of dioxane. After addition of trimethylsilyl azide (6.84 g, 59.4 mmol), the reaction mixture is heated at 80° C. for 2 h. The solvent is stripped off in vacuo, the residue is taken up in 200 ml of ether and treated with 0.78 g (43.4 mmol) of water. The mixture is stirred vigorously for 30 min and kept at 5° C. for 2 d. The precipitate is filtered off with suction and discarded. (The precipitate consists mainly of Example XIII). The filtrate is concentrated to a volume of about 50 ml and cooled to 0° C. for 12 h, whereupon 6-benzylidene-cyclopentano[3,4]oxazine-2,4-(1H)-dione (2.52 g) crystallises, the crystals are filtered off with suction and washed with a little ether and the solid is treated with 103 ml of 0.1N hydrochloric acid. The mixture is stirred at room temperature for 1 h and filtered, and the filtrate is concentrated in vacuo. The residue is dried in vacuo over $P_4O_{10}$.

Yield: 0.95 g (7%) of a 5:1 E/Z isomer mixture
M.p.: 234° C.

$^1$H NMR (DMSO-$d_6$); δ=2.70–3.55 (m, 5H), 3.70 (cm, 1H), 6.48 (s, 1H), 7.12–7.42 (m, 5H)

$C_{13}H_{15}NO_2 \times HCl$ (217.3×36.5).

Example 51

1,2-cis-2-Amino-4-difluoromethylene-cyclopentane-1-carboxylic acid hydrochloride

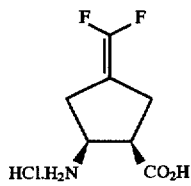

The title compound is prepared in analogy to the procedure of Example 2.

Yield: 1.26 g (96%)

M.p.: 215° C. (dec.)

$C_7H_9F_2NO_2 \times HCl$ (177.2–36.5)

Example 52

1,2-cis-2-Amino-4,4-difluoro-cyclopentane-1-carboxylic acid hydrochloride

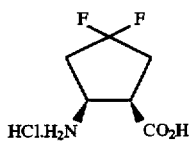

The title compound is prepared in analogy to the procedure of Example 2.

Yield: 1.85 g (83%)

M.p.: 222° C. (dec.)

$C_6H_9F_2NO_2 \times HCl$ (165.1×36.5)

Example 53

(−)-1,2-cis-2-Amino-4-methyl-cyclopentane-1-carboxylic acid hydrochloride

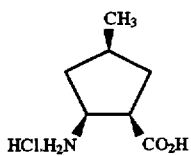

A solution of Example 32 (400 mg, 2.25 mmol) in 30 ml of EtOH and 5 ml of $H_2O$ is hydrogenated for 3 h at 3 bar and room temperature in the presence of 50 mg of palladium on active carbon (10%). The mixture is filtered through kieselguhr and the filtrate is concentrated in vacuo. The residue is dried at 25° C./0.1 mbar for 12 h.

Yield: 396 mg (98%) of a 5:1 diastereomer mixture on C-4

M.p.: 156° C.

$C_7H_{13}NO_2 \times HCl$ (143.2×36.5)

Example 54

(−)-1,2-cis-2-Amino-4-ethyl-cyclopentane-1-carboxylic acid hydrochloride

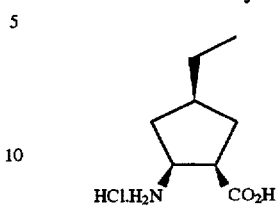

The title compound is prepared in analogy to the procedure of Example 53, starting from Example 34.

Yield: 140 g (93%) of a 16:1 diastereomer mixture

M.p.: 205° C. (dec.)

$C_8H_{15}NO_2 \times HCl$ (157.2×36.5)

Example 55

1,2-cis-2-Amino-4-benzyl-cyclopentane-1-carboxylic acid hydrochloride

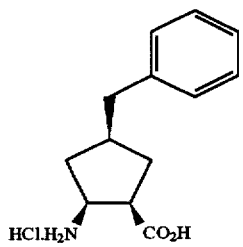

The title compound is prepared in analogy to the procedure of Example 53, starting from Example 50.

Yield: 198 mg (90%) of a 3:1 diastereomer mixture on C-4

M.p.: 104° C. (dec.)

$C_{13}H_{17}NO_2 \times HCl$ (219.3×36.5)

Example 56

1,2-cis-2-N-(tert-Butoxycarbonyl)amino-4-methylene-cyclopentane-1-carboxylic acid

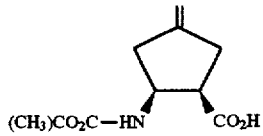

A solution of the compound from Example 2 (30.0 g, 170 mmol) in 350 ml of dioxane and 252 ml of 1N $Na_2CO_3$ solution is treated at 0° C. with di-tert-butyl dicarbonate (40.5 g, 185 mmol) and stirred at room temperature for 16 h. The dioxane is stripped off in vacuo and the aqueous residue is treated with 200 ml of ethyl acetate. The pH of the aqueous phase is adjusted to pH 2–3 by addition of 1N aqueous $KHSO_4$ solution. The organic phase is separated off and the aqueous phase is extracted with ethyl acetate (2×200 ml). The combined organic phases are washed with water (2×100 ml), dried over $Na_2SO_4$ and concentrated in vacuo.

Yield: 38.3 g (93%)

¹H (DMSO-d₆): δ=1.39 (s, 9H), 2.30–2.72 (m, 4H), 3.00 (dt, 1H), 4.12 (dt, 1H), 4.85 (s, 2H), 6.78 (d, 1H), 12.08 (s, 1H)

$C_{12}H_{19}NO_4$ (214.3)

Example 57

Methyl 1,2-cis-2-N-(tert-butoxycarbonyl)amino-4-methylene-cyclopentane-1-carboxylate

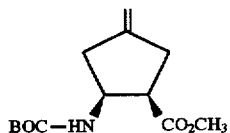

A solution of the compound from Example 56 (54.5 g, 226 mmol), methanol (21.8 g, 680 mmol) and 4-(N,N-dimethylamino)pyridine (2.76 g, 22.6 mmol) in 600 ml of $CH_2Cl_2$ is slowly treated at 0° C. with a solution of dicyclohexylcarbodiimide (51.4 g, 250 mmol) in 200 ml of $CH_2Cl_2$. After stirring at room temperature for 2 h, the mixture is filtered, and the filtrate is washed with 0.1N HCl (300 ml), satd. NaHCO₃ solution (300 ml) and water (300 ml), dried (Na₂SO₄) and concentrated in vacuo. The residue is chromatographed on silica gel (petroleum ether/ethyl acetate=3:1).

Yield: 42.0 g (73%)
M.p.: 55° C.
R_f=0.30 (petroleum ether/ethyl acetate=3:1)
$C_{13}H_{21}NO_4$ (255.3)

Example 58

Methyl 1,2-cis-2-N-(tert-butoxycarbonyl)amino-4-oxo-cyclopentane-1-carboxylate

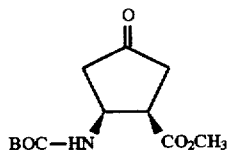

The title compound is prepared in analogy to the procedure of Example 4, starting from Example 57.

Yield: 34.4 g (92%)
M.p.: 135° C.
$C_{12}H_{19}NO_5$ (257.3)

Example 59

Methyl 1,2-cis-2-N-(tert-butoxycarbonyl)amino-4-oximino-cyclopentane-1-carboxylate

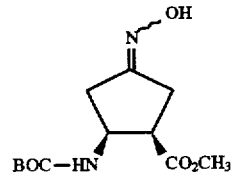

A solution of Example 58 (500 mg, 1.94 mmol), pyridine (0.80 ml, 9.80 mmol) and hydroxylamine hydrochloride (148 mg, 2.25 mmol) in 10 ml of EtOH is heated under reflux for 20 h. The solvent is stripped off in vacuo, the residue is taken up in water (20 ml) and the mixture is extracted with ether (3×20 ml). The combined ether phases are washed with water (1×10 ml), dried (Na₂SO₄) and concentrated in vacuo. The residue is chromatographed on silica gel (diethyl ether).

Yield: 269 mg (51%)

R_f=0.67/0.71 (diethyl ether)

$C_{12}H_{20}N_2O_5$ (272.3)

Example 60

Methyl 1,2-cis-2-amino-4-oximino-cyclopentane-1-carboxylate hydrochloride

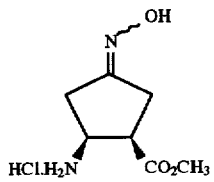

The title compound is prepared in analogy to the procedure of Example 5, starting from Example 59.

Yield: 103 mg (54%)

M.p.: 90°–95° C. (dec.)

$C_7H_{12}N_2O_3 \times HCl$ (223.1×36.5)

Example 61

Methyl 1,2-trans-2-N-(tert-butoxycarbonyl)amino-4-methylene-cyclopentane-1-carboxylate

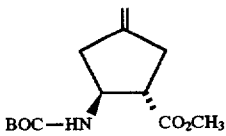

A solution of Example 57 (1.00 g, 3.9 mmol) and 1,8-diazabicyclo[5.4.0]undec-7-ene (0.90 g, 5.9 mmol) in 20 ml of MeOH is heated under reflux for 12 h. The solvent is stripped off in vacuo, the residue is taken up in ethyl acetate (30 ml), and the mixture is washed with 1N HCl (10 ml) and water (10 ml), dried (Na₂SO₄) and concentrated in vacuo. The residue is chromatographed in silica gel (petroleum ether/ethyl acetate=3:1).

Yield: 520 mg (52%)

M.p.: 140° C.

R_f=0.26 (petroleum ether/ethyl acetate=3:1)

$C_{13}H_{21}NO_4$ (255.3)

Example 62

Methyl 1,2-trans-2-amino-4-methylene-cyclopentane-1-carboxylate

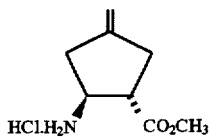

The title compound is prepared in analogy to the procedure of Example 37, starting from Example 61.

Yield: 141 mg (30%)

$^1$H NMR (DMSO): δ=2.30–2.50, 2.67–2.90 (2m, 4H), 3.08 (dt, 1H), 3.68 (s, 3H), 3.72 (dt, 1H), 4.95 (s, 2H), 8.40 (s, 3H)

$C_8H_{13}NO_2 \times HCl$ (155.2×36.5)

Example 63

Methyl 1,2-cis-2-N-(tert-butoxycarbonyl)amino-4-hydroxy-cyclopentane-1-carboxylate

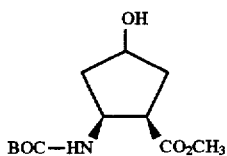

The title compound is prepared in analogy to the procedure of Example 7, starting from Example 58.

Yield: 3.30 g (97%) of a 3:1 diastereomer mixture $^1$H NMR (CDCl$_3$): δ=1.45 (s, 9H), 3.14 and 3.32 (2dt, 1H), 3.68 and 3.70 (2s, 3H), 4.40 and 4.46 (2dt, 1H), 5.40 (d, 1H)

$C_{12}H_{21}NO_5$ (259.3)

Example 64

Methyl 1,2-cis-2-N-(tert-butoxycarbonyl)amino-4-cyclopentene-1-carboxylate

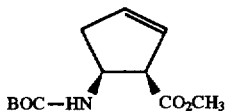

A solution of Example IV (3.90 g, 8.80 mmol) in 87 ml of THF is slowly treated at 0° C. with 30% strength H$_2$O$_2$ (5.23 g, 46.3 mmol) and stirred at room temperature for a further 3 h. After addition of 100 ml of ice-water, the mixture is extracted with CH$_2$Cl$_2$ (3×100 ml), and the combined organic phases are washed with satd. NaCl solution (100 ml), dried (Na$_2$SO$_4$) and concentrated in vacuo. The residue is chromatographed on silica gel (petroleum ether/diethyl ether=2:1, R$_f$=0.33). 1.32 g (62%) of a 35:65 mixture of the title compound and the corresponding 3-cyclopentene isomer are obtained. After fractional crystallisation from n-hexane (the title compound is found in the mother liquor in each case), the title compound is obtained.

Yield: 142 mg (7%)

$^1$H NMR (CDCl$_3$): δ=1.48 (s, 9H), 2.37, 2.70 (AB part of an ABX system, 2H), 3.70 (s, 3H), 3.71 (m, 1H), 4.62 (dt, 1H), 5.20 (d, 1H), 5.71 (m, 1H), 5.96 (m, 1H)

$C_{12}H_{19}NO_4$ (241.3)

Example 65

Methyl 1,2-cis-2-amino-4-cyclopentene-1-carboxylate hydrochloride

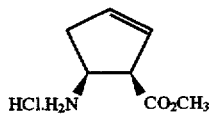

The title compound is prepared in analogy to the procedure of Example 5, starting from Example 64.

Yield: 93 mg (89%) $^1$H NMR (d$_6$-DMSO): δ=2.40–2.85 (m, 2H), 3.86 (m, 1H), 4.01 (dt, 1H), 5.76 (m, 1H), 5.97 (m, 1H), 8.10 (s, 3H)

$C_7H_{11}NO_2 \times HCl$ (141.2×36.5)

Example 66

Ethyl 1,2-cis-2-benzylamino-3-benzyloxymethyl-cyclo-pentane-1-carboxylate

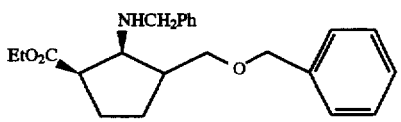

The title compound is prepared in analogy to the procedure of Example 10, starting from Example XXIII.

Yield: 8.38 (76%)

M.p.: 215° C. (dec.)

Diastereometer ratio D$_1$:D$_2$=6:1

F$_f$=0.43 (D$_1$), 0.34 (D$_2$), (petroleum ether/diethyl ether= 1:1)

$C_{24}H_{29}NO_3$ (379.50)

Example 67

Ethyl 1,2-cis-2-amino-3-hydroxymethyl-cyclopentane-1-carboxylate hydrochloride

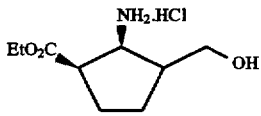

The title compound is prepared in analogy to the procedure of Example 13, starting from Example 66.

Yield: 3.14 g (97%)

Diastereomer ratio D$_1$:D$_2$=6:1

$^1$H NMR (CDCl$_3$): δ=1.28, 1.29 (2t, 3H), 1.72–2.30 (m, 4H), 2.71 (D$_2$) and 2.88 (D$_2$) (2m, 1H), 3.06 (D$_2$) and 3.27 (D$_2$) (2m, 1H), 3.50–3.90 (m, 3H), 4.10–4.32 (m, 3H), 8.40 (s, 3H)

$C_9H_{17}NO_3 \times HCl$ (187.2×36.5)

Example 68

Ethyl 1,2-cis-2-N-(tert-butoxycarbonyl)amino-3-hydroxy-methyl-cyclopentane-1-carboxylate

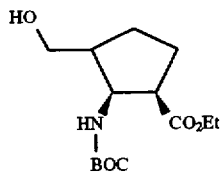

The title compound is prepared in analogy to the procedure of Example 3, starting from Example 67.

Yield: 2.98 g (98%)

Diastereomer ratio $D_1:D_2 = 5:1$ $^1$H NMR (CDCl$_3$): 1.28 (2t, 3H), 1.45 (2s, 9H), 1.65–2.38 (m, 5H), 3.02 (D$_2$), 3.06 (D$_1$), (2dt, 1H), 3.22–3.60 (m, 2H), 3.95–4.40 (m, 4H), 4.95 (D$_1$), 5.61 (D$_2$) (2d, 1H)

$C_{14}H_{25}NO_5$ (287.4)

Example 69

Ethyl 1,2-cis-2-N-(tert-butoxycarbonyl)amino-3-methylene-cyclopentane-1- carboxylate

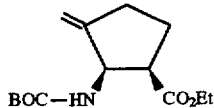

2-Nitrophenyl selenocyanate (3.56 g, 15.7 mmol) and a solution of tri-n-butylphosphine (3.17 g; 15.7 mmol) in 20 ml of THF are added dropwise under argon at room temperature to a solution of Example 68 (2.25 g, 7.83 mmol) in 210 ml of THF. After stirring for 30 min, 30% strength H$_2$O$_2$ (1.33 g, 39.2 mmol) is added dropwise and the mixture is stirred overnight at room temperature. After addition of water (500 ml), the mixture is extracted with ethyl acetate (3×250 ml), the combined organic phases are washed with NaHCO$_3$ solution (200 ml) and dried (MgSO$_4$) and the solvent is stripped off in vacuo. The residue is chromatographed on silica gel (petroleum ether/diethyl ether=2:1).

Yield: 1.67 g (79%)

M.p.: 64° C.

$C_{14}H_{23}NO_4$ (269.3)

Example 70

1,2-cis-2-N-(tert-Butoxycarbonyl)amino-3-methylene-cyclopentane-1-carboxylic acid

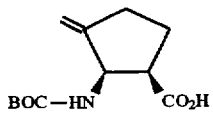

The title compound is prepared in analogy to the procedure of Example IX, starting from Example 69.

Yield: 1.71 g (97%)

M.p.: 135° C.

$C_{12}H_{19}NO_4$ (241.3)

Example 71

Methyl 1,2-cis-2-N-(tert-butoxycarbonyl)amino-3-methylene-cyclopentane-1-carboxylate

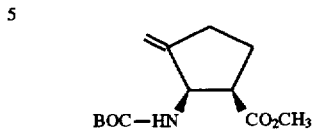

The title compound is prepared in analogy to the procedure of Example 57, starting from Example 70.

Yield: 1.59 g (91%)

M.p.: 44° C.

$C_{13}H_{21}NO_4$ (255.3)

Example 72

1,2-cis-2-Amino-3-methylene-cyclopentane-1-carboxylic acid hydrochloride

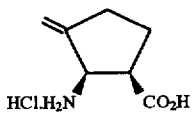

(tert-Butyldimethyl)silyl trifluoromethanesulphonate (1.64 g, 6.21 mmol) is added dropwise to a solution of Example 70 (500 mg, 2.07 mmol) and 2,6-lutidine (890 mg, 8.30 mmol) in 5 ml of CH$_2$Cl$_2$ at room temperature under argon. The mixture is stirred for 3 h, 10 ml of satd. NH$_4$Cl solution are added and the mixture is extracted with ether (2×20 ml), the combined organic phases are washed with satd. NaCl solution (10 ml) and dried (Na$_2$ SO$_4$), and the solvent is stripped off in vacuo. The residue is taken up in 20.7 ml of 0.1N hydrochloric acid and 20 ml of THF, the mixture is stirred for 20 h, the THF is stripped off in vacuo, the residue is washed with ether (10 ml) and the aqueous phase is concentrated in vacuo.

The residue is dissolved in 7 ml of propene oxide and the solution is heated under reflux for 30 min. The precipitated solid is filtered off with suction and washed with ether and the residue (136 mg) is taken up in 9.6 ml of 0.1N hydrochloric acid. The solvent is stripped off in vacuo and the residue is dried in vacuo over P$_4$O$_{10}$.

Yield: 190 mg (52%)

M.p.: 208° C. (dec.)

$C_7H_{11}NO_2 \times HCl$ (141.2×36.5)

Example 73

Methyl 1,2-cis-2-amino-3-methylene-cyclopentane-1-carboxylate hydrochloride

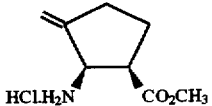

The title compound is prepared in analogy to the procedure of Example 37, starting from Example 71.

Yield: 145 mg (39%)

M.p.: 143° C.

$C_8H_{13}NO_2$ (155.2×36.5)

Example 74

Methyl 1,2-trans-2-N-(tert-butoxycarbonyl)amino-3-methylene-cyclopentane-1-carboxylate

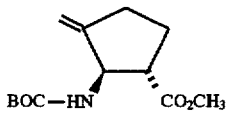

The title compound is prepared in analogy to the procedure of Example 61, starting from Example 71.
Yield: 410 mg (82%)
M.p.: 74° C.
$R_f$=0.43 (petroleum ether/ethyl acetate=3:1)
$C_{13}H_{21}NO_4$ (255.3)

Example 75

Methyl 1,2-trans-2-amino-3-methylene-cyclopentane-1-carboxylate hydrochloride

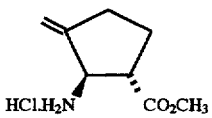

The title compound is prepared in analogy to the procedure of Example 37, starting from Example 74.
Yield: 228 mg (82%)
M.p.: 166° C.
$C_8H_{13}NO_2 \times HCl$ (155.2×36.5)

Example 76

Methyl 2-N-(tert-butoxycarbonyl)amino-cyclopentane-3-one-1-carboxylate

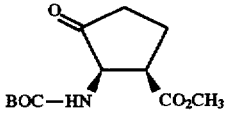

The title compound is prepared in analogy to the procedure of Example 4, starting from Example 71.
Yield: 898 mg (89%),
2 diastereomers cis:trans=2:1
M.p.: 98° C.
$C_{12}H_{19}NO_5$ (257.3)

Example 77

Methyl 2-amino-cyclopentan-3-one-1-carboxylate

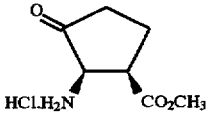

The title compound is prepared in analogy to the procedure of Example 5, starting from Example 76.

Yield: 139 mg (92%)
2 diastereomers cis:trans=2:1
M.p.: 250° C.
$C_7H_{11}NO_3 \times HCl$ (157.2×36.5)

Example 78

Methyl 2-N-(tert-butoxycarbonyl)amino-3,3-difluorecyclopentane-1-carboxylate

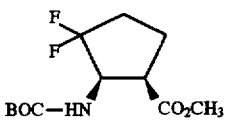

The title compound is prepared in analogy to the procedure of Example XVIII, starting from Example 76.
Yield: 176 mg (32%), cis:trans=2:1
$^1$H NMR (CDCl$_3$): δ=1.46 (s, 9H), 2.10–2.42 (m, 2H), 2.49–2.70 (m, 2H), 2.72 (dt, 2H), 3.72 (s, 3H), 4.30–4.52 (m, 1H), 4.85 (cis, s, 1H), 5.20 (trans, s, 1H) $C_{12}H_{19}F_2NO_4$ (279.3)

Example 79

Methyl 2-amino-3,3-difluoro-cyclopentane-1-carboxylate

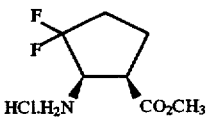

The title compound is prepared in analogy to the procedure of Example 5, starting from Example 78.
Yield: 61 mg (48%), cis:trans=2:1
M.p.: 118° C.
$C_7H_{11}F_2NO_2 \times HCl$ (176.2×36.5)

We claim:
1. A cyclopentane- or pentene-62-amino acid compound of the formula (I):

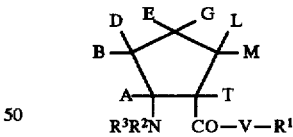

in which
A and T independently represent a substituent selected from the group consisting of hydrogen, fluorine, chlorine, bromine, methyl which is monosubstituted or disubstituted by identical or different hydroxyl or benzyloxy substituents, ethyl which is monosubstituted or disubstituted by identical or different hydroxyl, phenyl or benzyloxy substituents, and straight-chain or branched propyl or butyl which is optionally monosubstituted or disubstituted by identical or different hydroxyl, phenyl or benzyloxy substituents;

B and D independently represent a substituent selected from the group consisting of hydrogen, fluorine, chlorine, bromine, hydroxyl, methyl which is optionally monosubstituted or disubstituted by identical or different hydroxyl, phenyl or benzyloxy substituents, ethyl which is monosubstituted or disubstituted by identical or different hydroxyl, phenyl or benzyloxy substituents, and straight-chain or branched propyl or butyl which is optionally monosubstituted or disubstituted by identical or different hydroxyl, phenyl or benzyloxy substituents;

E, G, L and M independently represent a substituent selected from the group consisting of hydrogen, fluorine, chlorine, bromine, hydroxyl and alkyl having up to 4 carbon atoms which is optionally monosubstituted or disubstituted by identical or different hydroxyl, phenyl or benzyloxy substituents; or B and D, E and G in each case together represent a radical of the formula:

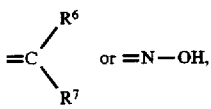

in which

R⁶ and R⁷ are identical or different and represent a substituent selected from the group consisting of hydrogen, fluorine, chlorine, bromine or straight-chain or branched alkyl having up to 4 carbon atoms or phenyl; or E and G and/or B and D together represent the radical of the formula:

B, D, E and G or E, G, L and M in each case together form a radical of the formula:

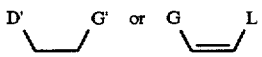

in which

D' and G' have the abovementioned meaning of D and G, but do not simultaneously represent hydrogen;

G and L are identical or different and denote hydrogen or methyl;

R² represents a substituent selected from the group consisting of hydrogen, allyloxycarbonyl, benzyl, benzyloxycarbonyl, Boc or Fmoc, straight-chain or branched alkyl having up to 4 carbon atoms, straight-chain or branched acyl having up to 4 carbon atoms, and an amino acid residue of the formula:

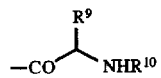

in which

R⁹ denotes hydrogen, straight-chain or branched alkyl having up to 4 carbon atoms or benzyl;

and

R¹⁰ denotes hydrogen, tert-butoxycarbonyl or Fmoc;

R³ represents hydrogen;

V represents a member selected from the group consisting of an oxygen atom, a sulphur atom and the —NH group;

R¹ represents a substituent selected from the group consisting of hydrogen and straight-chain or branched alkyl having up to 4 carbon atoms, and phenyl which are optionally substituted by fluorine, chlorine, bromine, nitro, cyano, methyoxy or ethoxy;

with the proviso that at least one of A, B, D, E, G, L, M and T is not hydrogen;

a stereoisomeric form of said compound, an acid addition salt thereof, or a metal salt complex thereof.

2. An antimicrobial composition comprising an antimicrobial effective amount of a cyclopentane- or pentene-β-amino acid compound according to claim 1 and a pharmaceutically acceptable carrier.

* * * * *